(12) United States Patent
Selvaraj et al.

(10) Patent No.: US 12,018,314 B2
(45) Date of Patent: Jun. 25, 2024

(54) ACCURATE MOLECULAR DECONVOLUTION OF MIXTURE SAMPLES

(71) Applicant: Arima Genomics, Inc., Carlsbad, CA (US)

(72) Inventors: Siddarth Selvaraj, San Diego, CA (US); Nathaniel Heintzman, San Diego, CA (US); Christian Edgar Laing, San Diego, CA (US)

(73) Assignee: Arima Genomics, Inc., Carlsbad, CA (US)

( * ) Notice: Subject to any disclaimer, the term of this patent is extended or adjusted under 35 U.S.C. 154(b) by 759 days.

(21) Appl. No.: 15/738,871

(22) PCT Filed: Jul. 4, 2016

(86) PCT No.: PCT/US2016/040921
§ 371 (c)(1),
(2) Date: Dec. 21, 2017

(87) PCT Pub. No.: WO2017/004612
PCT Pub. Date: Jan. 5, 2017

(65) Prior Publication Data
US 2018/0187241 A1    Jul. 5, 2018

Related U.S. Application Data

(60) Provisional application No. 62/188,355, filed on Jul. 2, 2015.

(51) Int. Cl.
*C12Q 1/6806* (2018.01)
*C12Q 1/6883* (2018.01)
(Continued)

(52) U.S. Cl.
CPC ......... *C12Q 1/6806* (2013.01); *C12Q 1/6883* (2013.01); *C12Q 1/6886* (2013.01);
(Continued)

(58) Field of Classification Search
CPC .. C12Q 1/6806; C12Q 1/6883; C12Q 1/6886; G16B 40/00; G16B 20/00
See application file for complete search history.

(56) References Cited

U.S. PATENT DOCUMENTS 8,071,296 B2    12/2011    Ruan et al.
9,434,985 B2    9/2016    Dekker et al.
(Continued)

FOREIGN PATENT DOCUMENTS

CN    102770558 A    11/2012
CN    104053789 A    9/2014
(Continued)

OTHER PUBLICATIONS

Wang et al., PennCNV: An integrated hidden Markov model designed for high-resolution copy number variation detection in whole-genome SNP genotyping data, 2007, Genome Research, 17, p. 1665-1674 (Year: 2007).*

(Continued)

*Primary Examiner* — Kaitlyn L Minchella
(74) *Attorney, Agent, or Firm* — Wolf, Greenfield & Sacks, P.C.

(57) ABSTRACT

The present disclosure relates to methods to deconvolute a mixture sample of genetic material from different origins or sources. The disclosed methods can be used in various applications, including, the non-invasive determination of a fetal genome, a fetal -ome (e.g. exome). or other targeted fetal locus from cell-free nucleic acids in maternal plasma or other body fluids; the determination of cancer-associated mutations from cell-free nucleic acids in a body fluid sample that contains a mixture of nucleic acids from normal cells and tumor cells; and quantification of donor cell contami- (Continued)

nation using a body fluid from a transplantation recipient to monitor and/or predict the outcome of a transplantation procedure.

6 Claims, 23 Drawing Sheets

(51) Int. Cl.
  *C12Q 1/6886*    (2018.01)
  *G16B 20/00*    (2019.01)
  *G16B 20/10*    (2019.01)
  *G16B 20/20*    (2019.01)
  *G16B 20/40*    (2019.01)
  *G16B 40/00*    (2019.01)

(52) U.S. Cl.
  CPC .............. *G16B 20/00* (2019.02); *G16B 20/10* (2019.02); *G16B 20/20* (2019.02); *G16B 20/40* (2019.02); *G16B 40/00* (2019.02); *C12Q 2600/156* (2013.01); *C12Q 2600/172* (2013.01)

(56) References Cited

U.S. PATENT DOCUMENTS

| | | |
|---|---|---|
| 9,663,826 B2 | 5/2017 | Barrett et al. |
| 9,708,648 B2 | 7/2017 | Dekker et al. |
| 9,715,573 B2 | 7/2017 | Putnam et al. |
| 10,318,706 B2 | 6/2019 | Putnam et al. |
| 2011/0287947 A1 | 11/2011 | Chen et al. |
| 2012/0095697 A1 | 4/2012 | Halpern et al. |
| 2012/0108460 A1 | 5/2012 | Quake et al. |
| 2012/0196754 A1 | 8/2012 | Quake et al. |
| 2013/0183672 A1 | 7/2013 | De Laat et al. |
| 2013/0196317 A1* | 8/2013 | Lapidus ............... C12Q 1/6883 435/6.11 |
| 2013/0316915 A1 | 11/2013 | Halpern et al. |
| 2014/0045705 A1 | 2/2014 | Bustamante et al. |
| 2016/0160275 A1 | 6/2016 | Ren et al. |
| 2016/0239602 A1 | 8/2016 | Shendure et al. |
| 2016/0246922 A1 | 8/2016 | Putnam et al. |
| 2017/0159109 A1 | 6/2017 | Zheng et al. |
| 2017/0300615 A1 | 10/2017 | Putnam et al. |
| 2017/0314014 A1 | 11/2017 | Green et al. |
| 2017/0335369 A1 | 11/2017 | Fields et al. |
| 2017/0362649 A1 | 12/2017 | Lieberman-Aiden et al. |
| 2018/0119203 A1 | 5/2018 | Rice et al. |
| 2018/0282796 A1 | 10/2018 | Ren et al. |
| 2019/0032113 A1 | 1/2019 | Troll et al. |
| 2019/0180843 A1 | 6/2019 | Putnam et al. |
| 2019/0279740 A1 | 9/2019 | Aiden et al. |

FOREIGN PATENT DOCUMENTS

| | | |
|---|---|---|
| EP | 2851431 A2 | 3/2015 |
| EP | 2 591 125 B1 | 4/2018 |
| WO | WO 2012/106546 A2 | 8/2012 |
| WO | WO 2013/177581 A2 | 11/2013 |
| WO | WO 2013/181367 A1 | 12/2013 |
| WO | WO 2014/144491 A1 | 9/2014 |
| WO | WO 2015/010051 A1 | 1/2015 |
| WO | WO 2016/061517 A2 | 4/2016 |
| WO | WO 2017/004612 A1 | 1/2017 |
| WO | WO 2017/058784 A1 | 4/2017 |
| WO | WO 2017/197300 A1 | 11/2017 |

OTHER PUBLICATIONS

Chen et al., Haplotype-assisted accurate non-invasive fetal whole genome recovery through maternal plasma sequencing, 2013, Genome Medicine, 5(18), p. 1-10 (Year: 2013).*

Kitzman et al., Noninvasive Whole-Genome Sequencing of a Human Fetus, 2012, Sci Transl Med, 4(137), supplemental information (Year: 2012).*

Lo et al., Maternal Plasma DNA Sequencing Reveals the Genome-Wide Genetic and Mutational Profile of the Fetus, 2010, Prenatal Diagnosis, 2(61), p. 1-13 (Year: 2010).*

Lau et al., Non-invasive prenatal testing for fetal chromosomal abnormalities by low-coverage whole-genome sequencing of maternal plasma DNA: review of 1982 consecutive cases in a single center, 2014, Ultrasound Obstet Gynecol, 43, p. 254-264 (Year: 2014).*

Straver et al., WISECONDOR: detection of fetal aberrations from shallow sequencing maternal plasma based on a within-sample comparison scheme, 2014, Nucleic Acids Research, 42(5), p. 1-9 (Year: 2014).*

"Extended European Search Report dated Jan. 8, 2019 in European Patent Application No. 16818949.6, filed on Jul. 4, 2016 and published as EP 3 317 420 on May 9, 2018", 6 pages.

"International Preliminary Report on Patentability, dated Jan. 11, 2018 in International Application No. PCT/US2016/040921, filed on Jul. 4, 2016 and published as WO 2017/004612 on Jan. 5, 2017", 7 pages.

"International Search Report and Written Opinion dated Oct. 4, 2016 in International Application No. PCT/US2016/040921, filed on Jul. 4, 2016 and published as WO 2017/004612 on Jan. 5, 2017", 11 pages.

Amini, et al., "Haplotype-Resolved Whole Genome Sequencing by Contiguity Preserving Transposition and Combinatorial Indexing", Nature Genetics, 2014, 46(12):1343-1349.

Bansal, Vikas, "Integrating Read-Based and Population-Based Phasing for Dense and Accurate Haplotyping of Individual Genomes", Bioinformatics, 2019, 35: i242-i248.

Belaghzal, et al., "Hi-C 2.0: An Optimized Hi-C Procedure for High-Resolution Genome-Wide Mapping of Chromosome Conformation", Methods, Jul. 1, 2017, 123:56-65.

Belton, et al., "Hi-C: A Comprehensive Technique to Capture the Conformation of Genomes", Methods, Nov. 2012, 58(3):16 pages.

Browning, et al., "Haplotype Phasing: Existing Methods and New Developments", Nature Reviews Genetics, 2011, 12(10):703-714.

Browning, et al., "Improving the Accuracy and Efficiency of Identity-by-Descent Detection in Population Data", Genetics, 2013, 194(2):459-471.

Browning, et al., "Rapid and Accurate Haplotype Phasing and Missing-Data Inference for Whole-Genome Association Studies by Use of Localized Haplotype Clustering", American Journal of Human Genetics, 2007, 81(5):1084-1097.

Cirulli, et al., "Uncovering the Roles of Rare Variants in Common Disease Through Whole-Genome Sequencing", Nature Reviews Genetics, 2010, 11:415-425.

Comet, et al., "A Chromatin Insulator Driving Three-Dimensional Polycomb Response Element (PRE) Contacts and Polycomb Association with the Chromatin Fiber", Proceedings of the National Academy of Sciences, 2011, 108(6):2294-2299.

Crawford, et al., "Definition and Clinical Importance of Haplotypes", Annual Review of Medicine, 2005, 56:303-320.

Dhallan, et al., "A Non-Invasive Test for Prenatal Diagnosis Based on Fetal DNA Present in Maternal Blood: A Preliminary Study", The Lancet, Mar. 2007, 369(9560):474-481.

Dudchenko, et al., "De Novo Assembly of the Aedes Aegypti Genome Using Hi-C Yields Chromosome-Length Scaffolds", Science, Apr. 7, 2017, 356:92-95.

Eddy, Sean R., "What Is a Hidden Markov Model?", Nature Biotechnology, 2004, 22:1315-1316.

Erythematosus, et al., "Genome-Wide Association Scan in Women with Systemic Lupus Erythematosus Identifies Susceptibility Variants in ITGAM, PXK, KIAA1542 and Other Loci", Nature Genetics, 2008, 40(2):204-210.

Fosler-Lussier, Eric, "Markov Models and Hidden Markov Models: A Brief Tutorial", International Computer Science Institute, Dec. 1998, 1-7.

Fu, et al., "Protein-Mediated 3D Genome Architecture by HiChIP", Oklahoma Medical Research Foundation, 2017, 1 page.

(56) References Cited

OTHER PUBLICATIONS

Genomes Project, et al., "A Map of Human Genome Variation from Population Scale Sequencing", Nature, 2010, 467(7319):1061-1073.
Genomes Project, et al., "An Integrated Map of Genetic Variation From 1,092 Human Genomes", Nature, 2012, 491(7422):56-65.
Ghurye, et al., "Integrating Hi-C Links with Assembly Graphs for Chromosome-Scale Assembly", PLOS Computational Biology, 2018, 15(8):9 pages.
Ghurye, et al., "Scaffolding of Long Read Assemblies Using Long Range Contact Information", BMC Genomics, 2017, 18(527):11 pages.
Hindorff, et al., "Potential Etiologic and Functional Implications of Genome-Wide Association Loci for Human Diseases and Traits", Proceedings of the National Academy of Sciences, 2009, 106(23):9362-9367.
Hsieh, et al., "Mapping Nucleosome Resolution Chromosome Folding in Yeast by Micro-C", Cell, Jul. 2, 2015, 162(1):108-119.
Hsieh, et al., "Micro-C XL: Assaying Chromosome Conformation at Length Scales from the Nucleosome to the Entire Genome", Nature Methods, 2016, 13(12):1009-1011.
Kitzman, et al., "Noninvasive Whole-Genome Sequencing of a Human Fetus", Science Translational Medicine, Jun. 6, 2012, 4(137-140):115-122.
Kong, et al., "Parental Origin of Sequence Variants Associated with Complex Diseases", Nature, 2009, 462(7275):868-874.
Lai, et al., "Trac-Looping Measures Genome Structure and Chromatin Accessibility", Nature Methods, 2018, 15(9):741-747.
Lieberman-Aiden, et al., "Comprehensive Mapping of Long-Range Interactions Reveals Folding Principles of the Human Genome", Science, Oct. 2009, 326(5950):289-293.
Ma, et al., "Fine-Scale Chromatin Interaction Maps Reveal the Cis-Regulatory Landscape of Human lincRNA Genes", Nature Methods, Jan. 2015, 12(1):71-78.
Meyer, et al., "A High Coverage Genome Sequence from an Archaic Denisovan Individual", Science, 2012, 338(6104):222-226.
Musone, et al., "Multiple Polymorphisms in The TNFAIP3 Region Are Independently Associated with Systemic Lupus Erythematosus", Nature Genetics, 2008, 40(9):1062-1064.
Nagano, et al., "Comparison of Hi-C Results Using in-Solution Versus In-Nucleus Ligation", Genome Biology, 2015, 16(175):13 pages.
Nagano, et al., "Single Cell Hi-C Reveals Cell-To-Cell Variability in Chromosome Structure", Nature, Oct. 2013, 502(7469):59-64.
Ng, et al., "Exome Sequencing Identifies the Cause of a Mendelian Disorder", Nature Genetics, 2010, 42(1):30-35.
Olivares-Chauvert, et al., "Capturing Pairwise and Multi-Way Chromosomal Conformations Using Chromosomal Walks", Nature, 2016, 540(7632):296-300.
Pelikan, et al., "Enhancer Histone-Qtls are Enriched on Autoimmune Risk Haplotypes and Influence Gene Expression Within Chromatin Networks", Nature Communications, 2018, 9(2905):14 pages.
Petersdorf, et al., "MHC Haplotype Matching for Unrelated Hematopoietic Cell Transplantation", PLoS Medicine, Jan. 2007, 4(1):10 pages.
Ramani, et al., "Massively Multiplex Single-cell Hi-C", Nature Methods, 2017, 14(3):263-266.
Rao, et al., "A Three-Dimensional Map of the Human Genome at Kilobase Resolution Reveals Principles of Chromatin Looping", Cell, 2014, 159(7):1665-1680.
Rowley, et al., "Evolutionarily Conserved Principles Predict 3D Chromatin Organization", Molecular Cell, Sep. 7, 2017, 67:837-852.
Sanyal, et al., "The Long-Range Interaction Landscape of Gene Promoters", Nature, 2012, 489(7414):109-113.
Selvaraj, et al., "Complete Haplotype Phasing of the MHC and KIR Loci with Targeted Haploseq", BMC Genomics, 2015, 16(900):7 pages.
Selvaraj, et al., "Whole-Genome Haplotype Reconstruction Using Proximity-Ligation and Shotgun Sequencing", Nature Biotechnology, 2013, 31(12):1111-1118.
Snyder, et al., "Haplotype-Resolved Genome Sequencing: Experimental Methods and Applications", Nature Reviews Genetics, 2015, 16:344-358.
Studies, et al., "Replicating Genotype-Phenotype Associations", Nature, 2007, 447:655-660.
Tang, et al., "Advances in Genomic Profiling and Analysis of 3D Chromatin Structure and Interaction", Genes, 2017, 8(223):15 pages.
The International Hapmap Consort, et al., "A Second Generation Human Haplotype Map of Over 3.1 Million Snps", Nature, 2007, 449(7164):851-861.
Vitak, et al., "Construction of Thousands of Single Cell Genome Sequencing Libraries Using Combinatorial Indexing", bioRxiv, Jul. 23, 2016, 18 pages.
Yoon, Byung-Jun, "Hidden Markov Models and their Applications in Biological Sequence Analysis", Current Genomics, 2009, 10(6):402-415.
Zoltan, et al., "Hidden Markov Models in Bioinformatics", 2006, 37 pages.
Zschocke, J., "Dominant Versus Recessive: Molecular Mechanisms in Metabolic Disease", Journal of Inherited Metabolic Disease, 2008, 31(5):599-618.

* cited by examiner

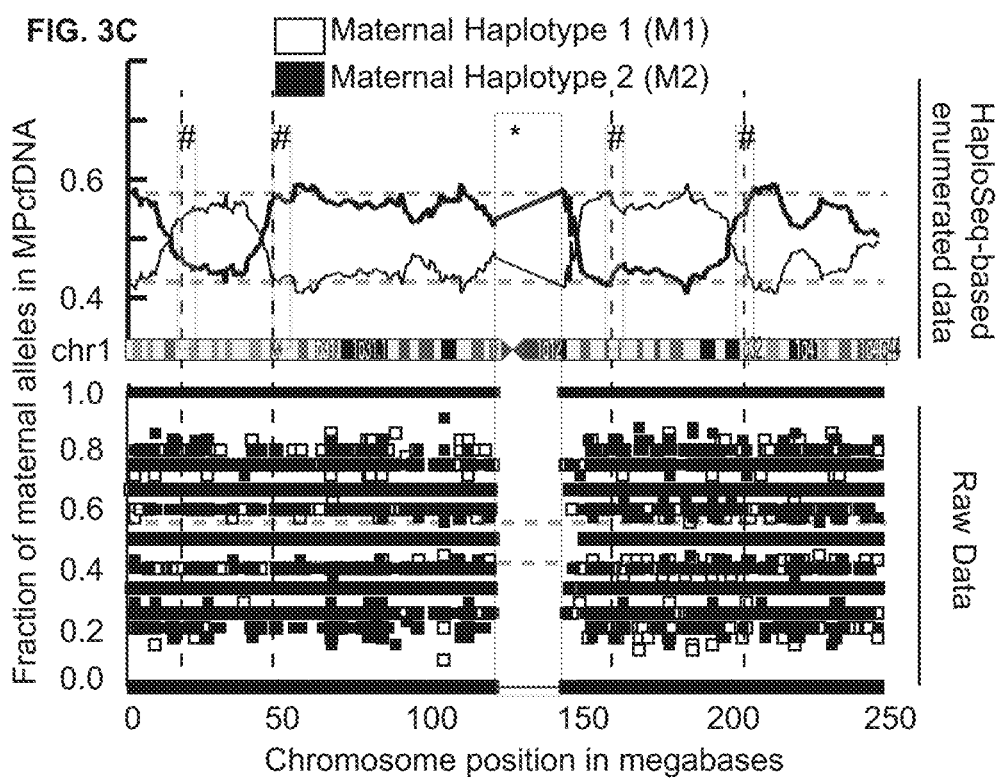

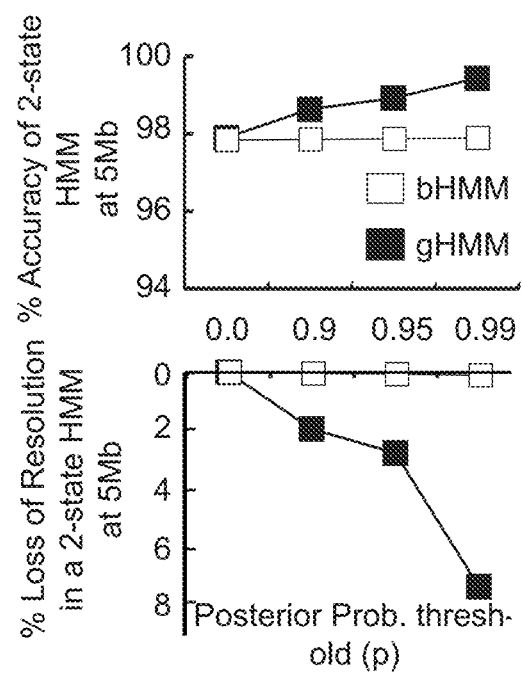

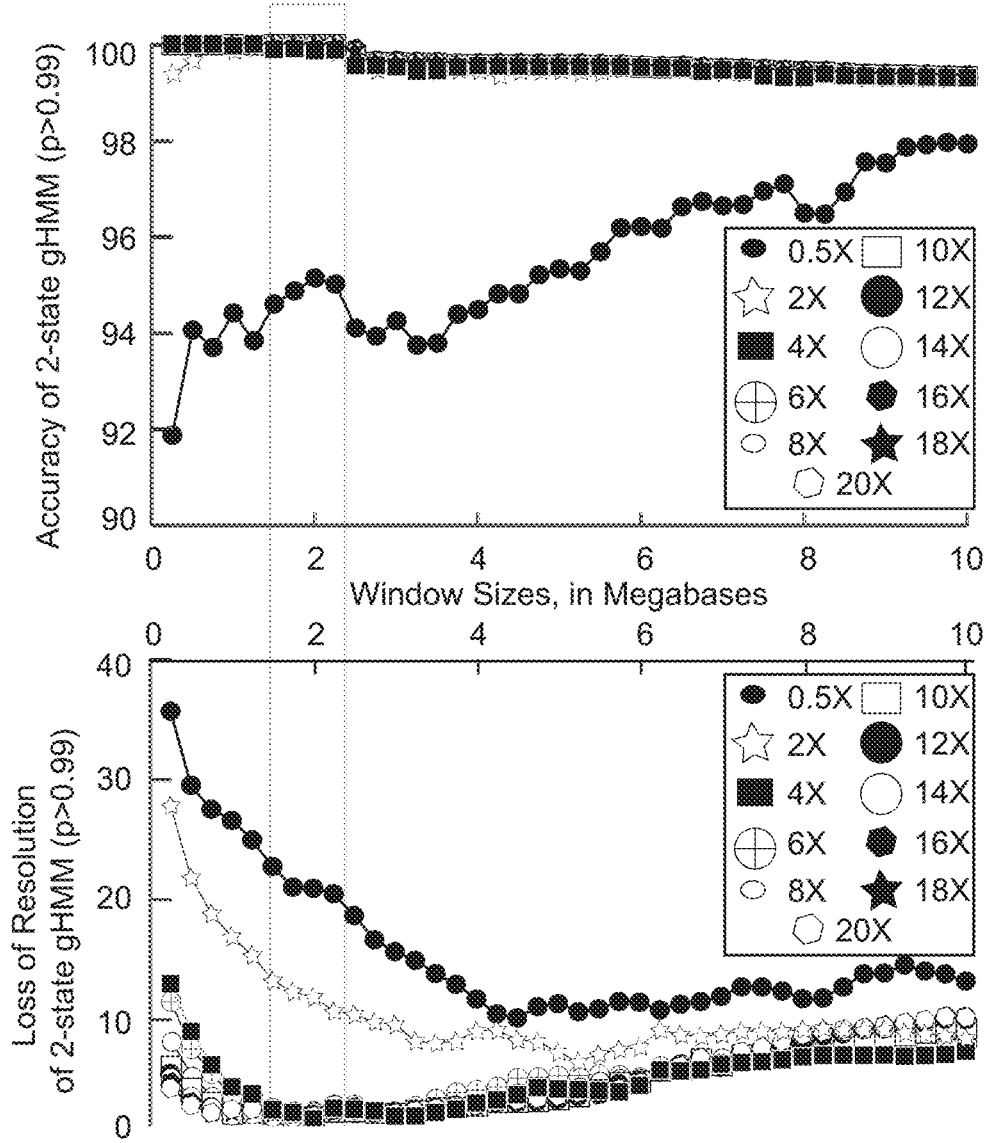

FIG. 4F
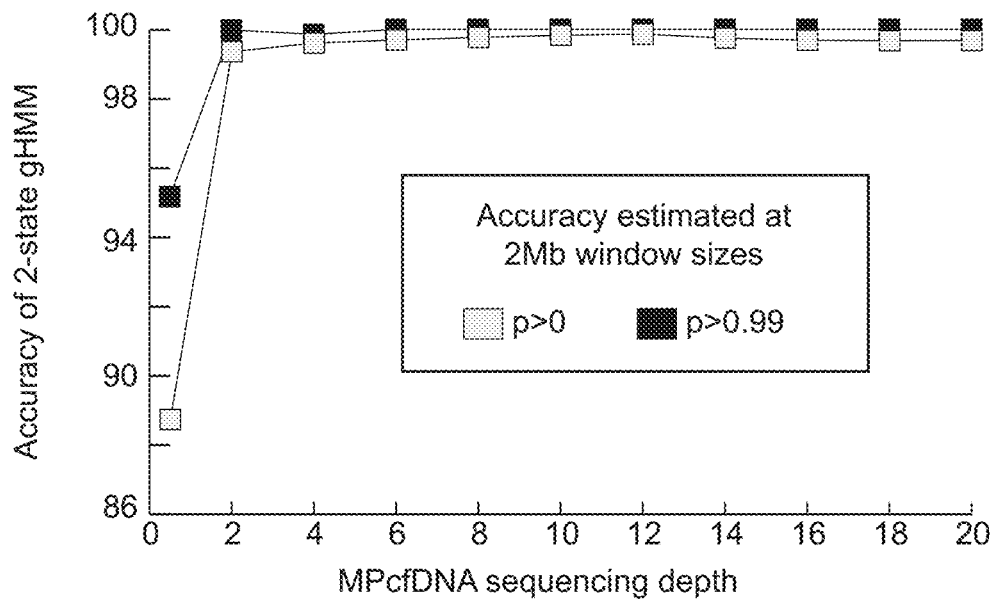
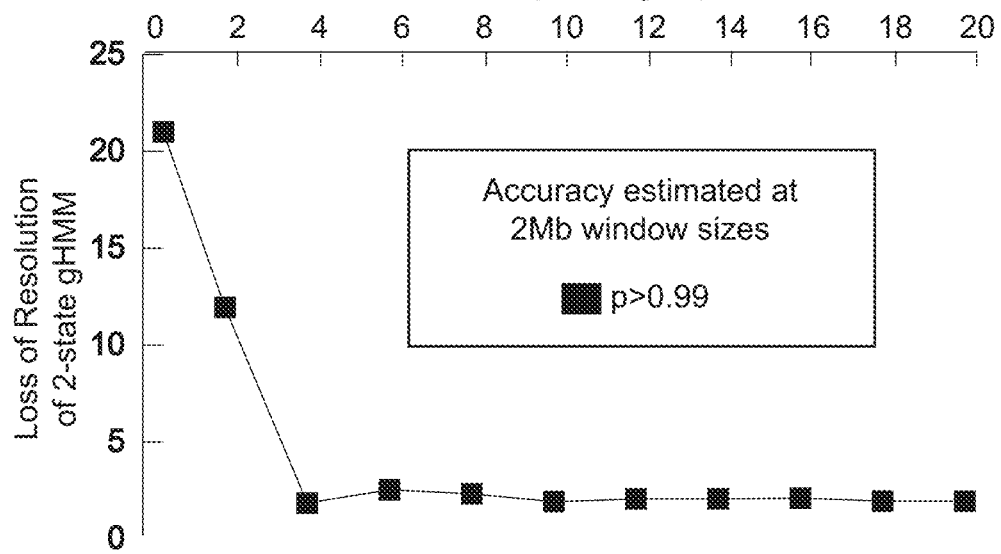

| Type | | Condition | Exp. Allele Fractions | HMM-States |
|---|---|---|---|---|
| Mat-Het Pat-Hom | (1) | Paternal allele Homozygous to Maternal Transmitted allele (MHet-PeqMT) | $(0.5 + f/2, 0.5 - f/2)$ | 2-state (M1, M2) |
| | (2) | Paternal allele Homozygous to Maternal un-transmitted allele | $(0.5, 0.5)$ | |
| Mat-Hom Pat-Het | (1) | Maternal allele Homozygous to Paternal Transmitted allele | $(1, 0)$ | 2-state (P1, P2) |
| | (2) | Maternal allele Homozygous to Paternal un-transmitted allele | $(0.5+0.5-f/2, f/2)$ | |
| Mat-Het Pat-Het | (1) | Mat. Transmitted equivalent to Pat. Transmitted allele. Fetus Homozygous | $(0.5 + f/2, 0.5 - f/2)$ | 4-state (M1P1, M2P1, M1P2, M2P2) |
| | (2) | Mat. Transmitted not equivalentt to Pat. Transmitted allele. Fetus Hetrozygous | $(0.5, 0.5)$ | |

FIG. 5

FIG. 6B
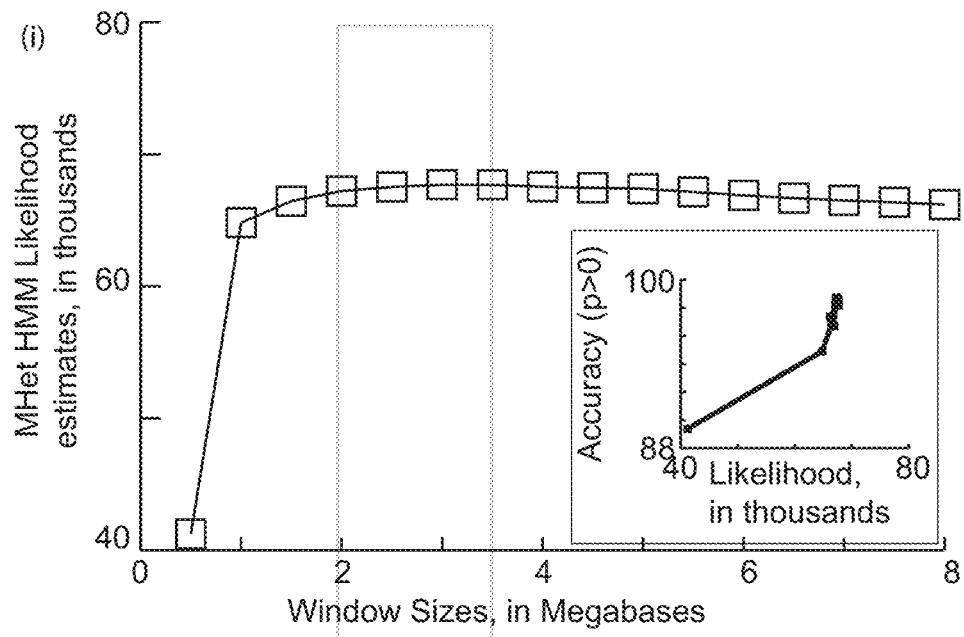
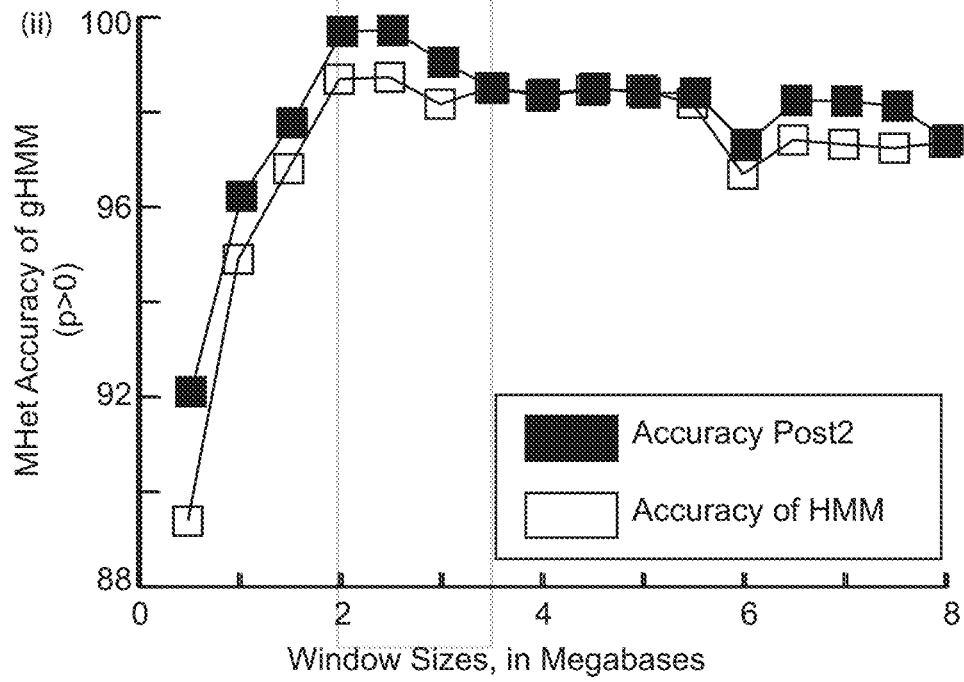

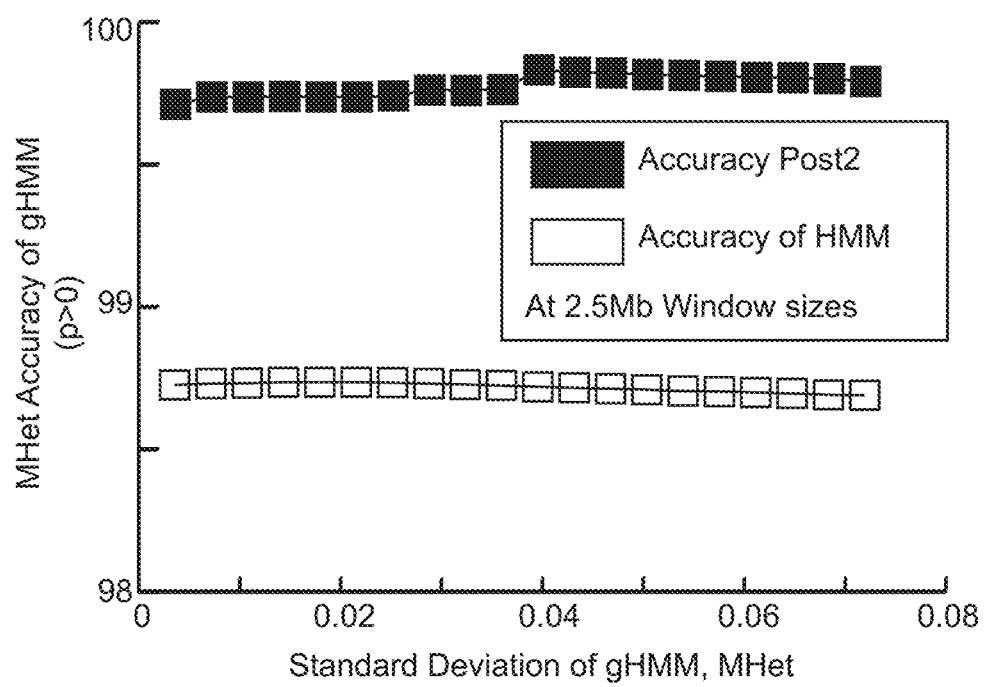

| Bases total (T) | Resolution (R): # Bases where model determines fetal bases | Accuracy (A): Fetal bases accurately determined among R | Theta: posterior threshold to define R, A. If theta = 0, R = 100% |
|---|---|---|---|
| Std. Deviation (Stdev) of the gaussian emission in HMM | Transition Matrix (TMM) for the gaussian HMM | Post-step1 window (PSW1) size to rectify minor switches | Post2 analyses to reduce any conflict between predictions from each allele type |

MHet.
HMM
Am = 98.73% (60135/60909)
Rm = 100.0% (60909/60909)
theta 0.99, Stdev 0.0036
TMM 0.0005, WS 2.5Mb post1
Am1 = 99.62% (60677/60909)
Rm1 = 100.0% (60909/60909)
PWS 500000 post2
Acm = 99.80% (95566/95753)
Rcm = 99.58% (95753/96160)

PHet.
HMM
Ap = 99.83% (61671/61775)
Rp = 100.0% (61775/61775)
theta 0.99, Stdev 0.00064
TMM 0.0001, WS 2.5Mb post1
Ap1 = 99.82% (61666/61775)
Rp1 = 100.0% (61775/61775)
PWS 100000

A = 99.77% (157162/157526)
R = 99.74% (157526/157935)

Bi-Het.
HMM
Ab = 98.11% (34186/34844)
Rb = 98.85% (34844/35251)
theta 0.99, Stdev 0.0024
TMM 0.0005
WS 3Mb (mat.), 2.5Mb (pat.)

post1
Ab1 = 98.63% (34367/34844)
Rb1 = 98.85% (34844/35251)
PWS 100000 (mat.), 500000 (pat.)

post2
Acp = 99.75% (96463/96704)
Rcp = 99.67% (96704/97026)

FIG. 7

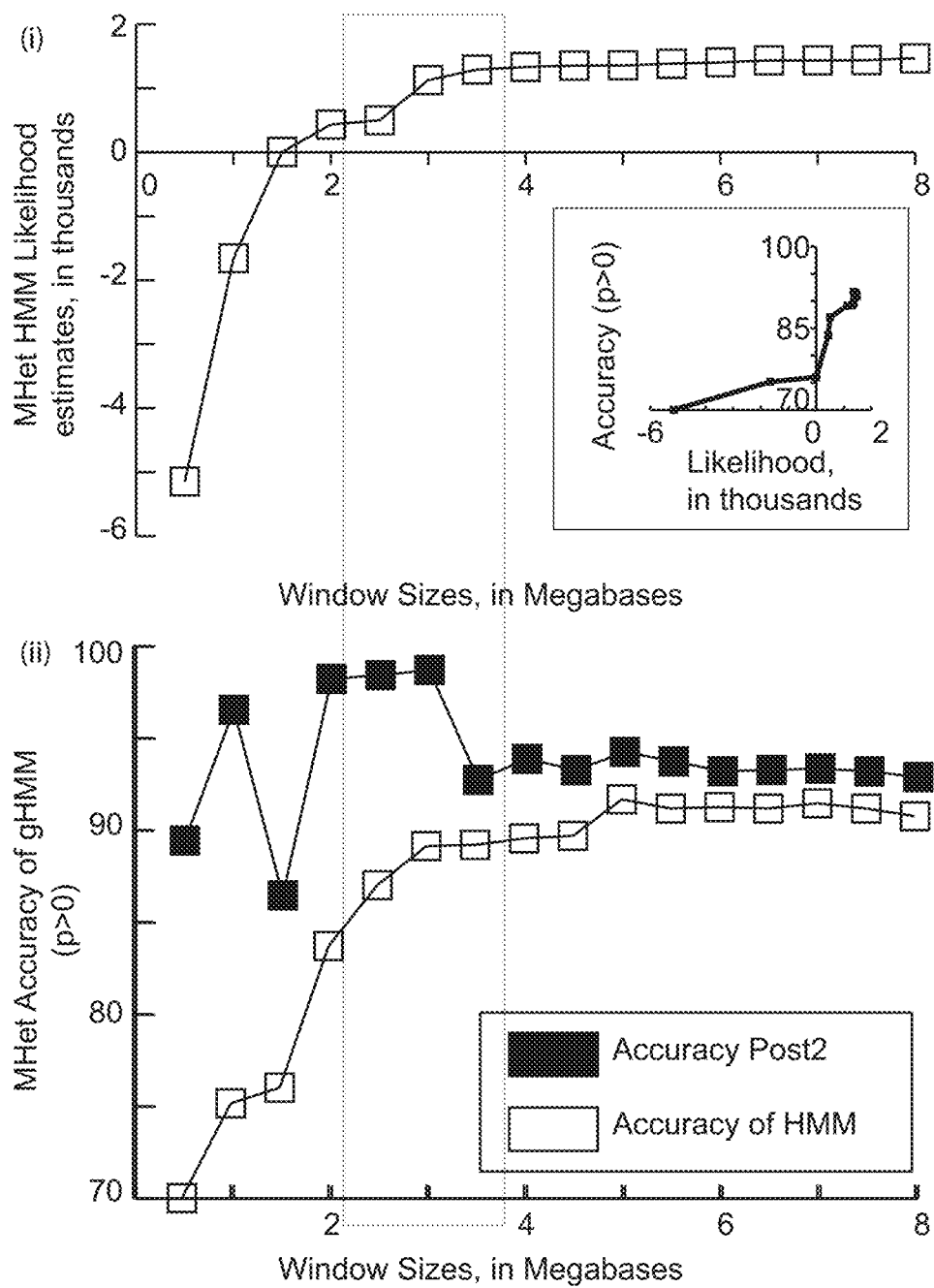

| Bases total (T) | Resolution (R): # Bases where model determines fetal bases | Accuracy (A): Fetal bases accurately determined among R | Theta: posterior threshold to define R, A. If theta = 0, R = 100% |
|---|---|---|---|
| Std. Deviation (Stdev) of the gaussian emission in HMM | Transition Matrix (TMM) for the gaussian HMM | Post-step1 window (PSW1) size to rectify minor switches | Post2 analyses to reduce any conflict between predictions from each allele type |

MHet.
HMM:
Am = 91.29% (1247/1366)
Rm = 96.40% (1366/1417)
theta 0.99, Stdev 0.0036
TMM 0.01, WS 3Mb post1:
Am1 = 96.27% (1315/1366)
Rm1 = 96.40% (1366/1417)
PWS 60 alleles post2
Acm = 97.51% (1878/1926)
Rcm = 92.95% (1926/2072)

PHet.
HMM:
Ap = 99.35% (1376/1385)
Rp = 100.0% (1385/1385)
theta 0.99, Stdev 0.00064
TMM 0.0001, WS 3Mb post1:
Ap1 = 99.71% (1381/1385)
Rp1 = 100.0% (1385/1385)
PWS 60 alleles

A = 99.12% (3282/3311)
R = 95.86% (3311/3454)

Bi-Het.
HMM:
Ab = 86.04% (567/659)
Rb = 83.95% (659/785)
theta 0.99, Stdev 0.0024
TMM 0.01
WS 3Mb (mat.,pat.)

post1:
Ab1 = 88.92% (586/659)
Rb1 = 83.95% (659/785)
PWS 60 alleles (mat., pat.)

post2
Acp = 99.80% (2040/2044)
Rcp = 94.32% (2044/2167)

FIG. 9

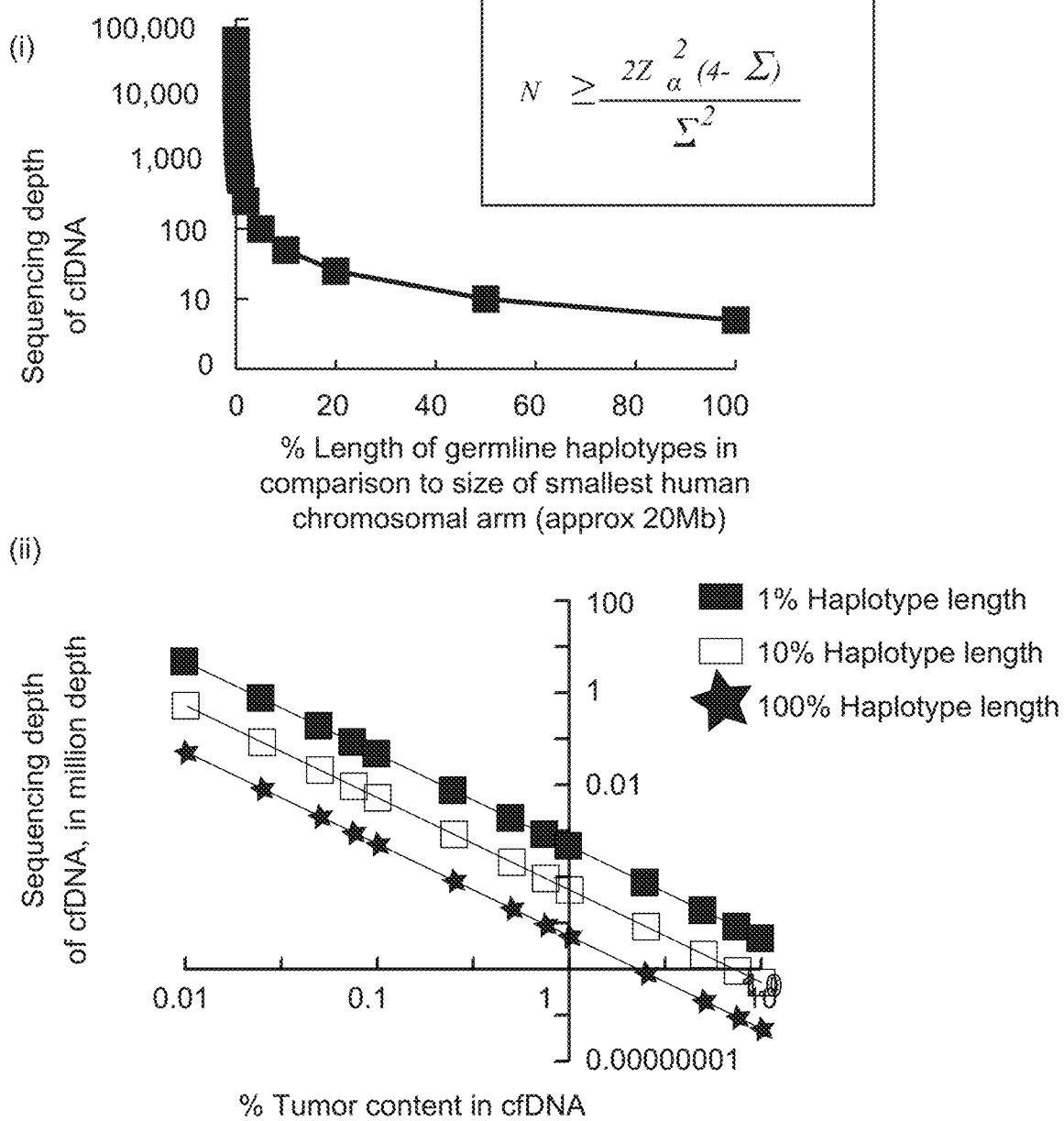

FIG. 12C
(i)
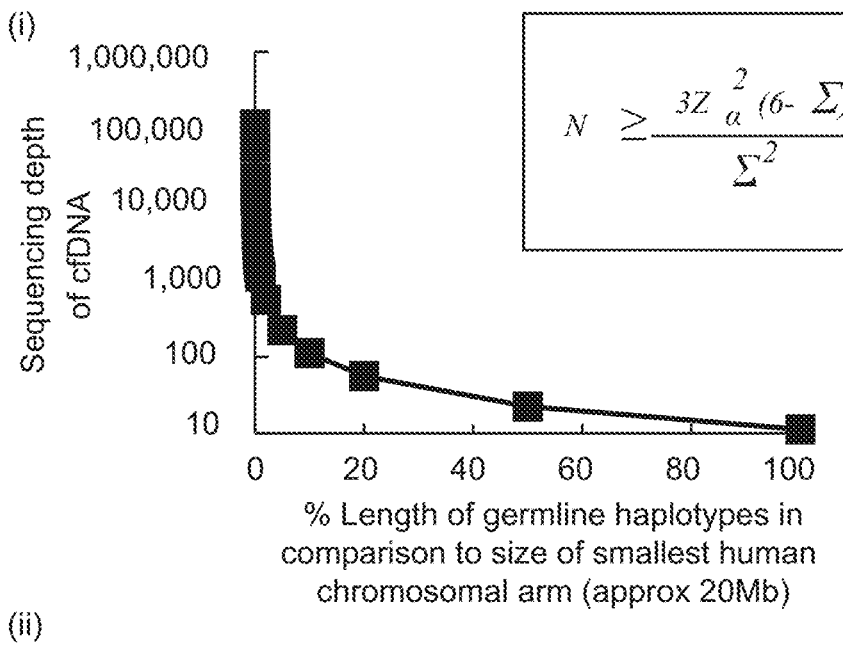
% Length of germline haplotypes in comparison to size of smallest human chromosomal arm (approx 20Mb)
(ii)
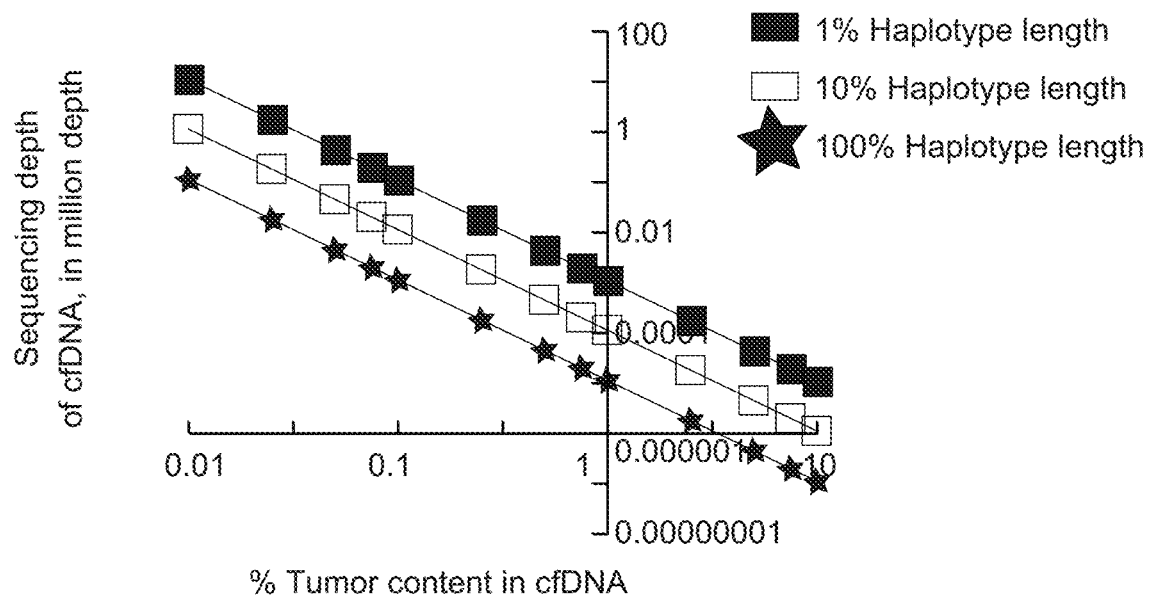
% Tumor content in cfDNA

ACCURATE MOLECULAR DECONVOLUTION OF MIXTURE SAMPLES

This patent application is a national stage of international patent application number PCT/US2016/040921, filed on Jul. 4, 2016, entitled ACCURATE MOLECULAR DECONVOLUTION OF MIXTURE SAMPLES, naming Siddarth SELVARAJ, Nathaniel HEINTZMAN and Christian Edgar LAING as inventors, which claims the benefit of U.S. Provisional Application No. 62/188,355, filed Jul. 2, 2015, entitled WHOLE GENOME DIPLOID SEQUENCE DETERMINATION OF THE FETUS, which is herein incorporated by reference in its entirety for all purposes.

STATEMENT OF GOVERNMENTAL SUPPORT

This invention was made with Government support under Grant Number 1R43HD087113-01A1 awarded by the National Institutes of Health. The Government has certain rights in the invention.

INTRODUCTION

This disclosure relates to methods to deconvolute a sample containing a mixture of genetic material from different origins or sources (referred to as a mixture sample or an impure sample). The disclosed methods can be used in various applications, including, but not limited to: a) the non-invasive determination of a fetal genome, a fetal -ome such as exome, or other targeted fetal locus from cell-free nucleic acids in maternal plasma or other body fluid; b) determination of tumor-associated nucleic acids from cell-free nucleic acids in a body fluid sample that contains a mixture of nucleic acids from normal cells and tumor cells; and c) quantification of donor genetic contamination using a body fluid from a transplantation recipient, to monitor and/or predict the outcome of a transplantation procedure.

BACKGROUND OF THE DISCLOSURE

There are several examples in nature and in medicine, where nucleic acids originating from different sources are mixed together and represented as a single sample. Deconvoluting such a mixture sample is fundamental to several clinical applications, and is extremely challenging.

One example of a mixed sample is cell-free nucleic acids from maternal body fluids such as plasma. Cell-free nucleic acids from maternal plasma contains a mixture of genetic material derived from both the mother and the fetus, and an accurate delineation of this mixture allows for the precise determination of the fetal genetic content to the level of single nucleotide variation (SNV) of genotypes and haplotypes using a simple maternal phlebotomy (blood draw), obviating the need for more invasive sampling methods. There are several thousand single-gene Mendelian disorders that cumulatively affect ~1% of human births, and in addition, micro-deletions, large megabase-scale aneuploidies, and trisomies contribute substantially to fetal genetic disorders. Together, these genetic defects are among the leading causes of both miscarriages and congenital birth disorders.

As second example of a mixed sample is cell-free nucleic acids from a patient who is being screened, tested, treated, or monitored for the presence of a tumor-associated mutation or abnormality. This type of mixed sample will contain nucleic acids from normal cells and tumor cells.

A third example of a mixed sample is cell-free nucleic acids from a transplantation recipient patient. This type of mixed sample will have recipient and donor nucleic acids. Quantifying the amount of donor genetic contamination will greatly assist in understanding the transplantation outcome, and/or monitoring of the transplantation procedure.

Therefore, a cost-effective, faster, and highly accurate method for deconvoluting mixture samples, such as the cell free nucleic acids described above, or any other mixture samples, to determine the genetic content, will have immense clinical utility.

SUMMARY OF THE DISCLOSURE

This disclosure addresses the above-mentioned unmet needs by providing a method for cost-effective deconvolution of a mixture sample, such as cell-free nucleic acids (cfNA such as cfDNA), for various clinical settings including: a) deconvolution of a maternal plasma cfDNA (MPcfDNA) sample to non-invasively determine the entire fetal genome (genotypes and haplotypes) by leveraging parental long haplotypes, for example, chromosome-spanning haplotypes in combination with low-depth (<10x) MPcfDNA sequencing; b) deconvolution of MPcfDNA to non-invasively determine the fetal -omes sequence (exomes or other -omes such as a common variants set or set of cis-regulatory elements, condition-specific gene panels, etc.) by leveraging parental long haplotypes, for example, chromosome-spanning haplotypes of -omes in combination with minimal sequencing of the MPcfDNA -omes; c) deconvolution of MPcfDNA to non-invasively determine a user-defined target fetal locus sequence by leveraging parental long haplotypes, for example, locus-spanning haplotypes of corresponding locus in combination with the sequencing of MPcfDNA representing the target locus, where the sequencing depth depends on the length of the locus; d) deconvolution of cfDNA to detect tumor-associated mutations by leveraging germline haplotypes in combination with cfDNA sequencing for cancer detection, monitoring and surveillance; e) deconvolution of recipient cfDNA (RcfDNA) by leveraging recipient haplotypes in combination with RcfDNA sequencing to quantify donor contamination to understand transplantation outcome, and/or monitoring, and (f) other utilities.

One embodiment of the disclosure comprises the use of HaploSeq (as described in S. Selvaraj, et al., Nature Biotechnology, "Whole genome haplotype reconstruction using proximity-ligation and shotgun sequencing", published online 3 Nov. 2013, doi:10.1038/nbt.2728; Selvaraj, et al. BMC Genomics, "Complete haplotype phasing of the MHC and KIR loci with targeted HaploSeq", published online 5 Nov. 2015, doi: 10.1186/s12864-015-1949-7; US Publication No. 2016/0160275 entitled "Whole-genome and targeted haplotype reconstruction"; and U.S. Provisional Patent Application (Application No. 62/234,329, filed Sep. 29, 2015) entitled "Whole-exome haplotype reconstruction"), to determine parental haplotypes and/or germline haplotypes of chromosome-spanning lengths, or other targeted lengths. The contents of these references are incorporated by reference in their entireties.

Another embodiment of the disclosure is to sequence the mixture sample—for example, cfNA—MPcfDNA, or cfDNA from a cancer patient, or RcfDNA. The fetal fraction present in MPcfDNA, or the tumor fraction present in a cancer patient's cfDNA, or the donor fraction in RcfDNA, is generally a minority: 5-15% in the fetal case, and 0.01-10% in both the cancer and transplantation cases.

Another embodiment of the disclosure is a novel HMM-based analysis, which is used to deconvolute the mixture sample by leveraging the parental and/or germline haplotypes. The disclosure features an innovative HMM-based analysis where the mixture data (e.g. cfDNA data) from nearby bases on the same haplotype is used to cumulatively support the decision to deconvolute a base. Such cumulative support from data on the same haplotype (referred to as "enumeration") reduces variance of observed allele fractions manifested in a mixture sample, which enables accurate deconvolution of a mixture sample via minimized mixture sample sequencing, thereby enabling cost-effective deconvolution of mixture samples. For instance, enumeration has allowed reducing the required sequencing depth of MPcfDNA from 40-70× depths to <10× depth in the case of determining an entire fetal genome. Haplotype-based enumeration allows for cost-effective and accurate deconvolution of a mixed or impure sample.

Disclosed herein are methods for non-invasive determination of fetal genetic content, comprising: obtaining a cellular maternal sample comprising a set of chromosomes having genomic DNA and obtaining maternal genotypes or haplotypes from the maternal sample; obtaining a cellular paternal sample comprising a set of chromosomes having genomic DNA, and obtaining paternal genotypes or haplotypes from the paternal sample; obtaining a cell-free nucleic acid maternal sample and determining the sequence of the cell-free nucleic acid maternal sample; determining fetal allele fractions of both transmitted and untransmitted maternal and paternal alleles by analyzing the sequencing data from the cell-free nucleic acid maternal sample; enumerating each fetal allele from neighboring fetal alleles; and inputting one or more enumerated alleles into a HMM to determine the fetal genetic content. In another embodiment, the method further comprising post-HMM analysis. In another embodiment, the sequencing is whole genome sequencing of the cell-free nucleic acid maternal sample, the maternal or paternal haplotypes are long, and the fetal genetic content is a whole fetal genome. In another embodiment, the long haplotypes are chromosome-spanning haplotypes. In yet another embodiment, the sequencing is -ome sequencing of the cell-free nucleic acid maternal sample, the maternal or paternal haplotypes are long, and the fetal genetic content is a fetal -ome. In another embodiment, the long haplotypes are chromosome-spanning haplotypes of -omes. In one embodiment, the -ome is an exome. In another embodiment, the sequencing is locus sequencing of the cell-free nucleic acid maternal sample, the maternal or paternal haplotypes are long, and the fetal genetic content is a fetal locus. In one embodiment, the long haplotypes are locus-spanning haplotypes. In other embodiments, an enumeration window size is from about 100 Kilobases to about 20 Megabases; or the fetal genetic content is determined at an accuracy rate of about 85% to 90%, 90% to 95%, 95% to 96%, 96% to 97%, 97% to 98%, 98% to 99%, or 99% to 100%; or the maternal sample, the paternal sample, and the cell-free nucleic acid maternal sample are from a human, a non-human mammal, an invertebrate, a plant, or a fungi. In yet other embodiments, the determination of fetal genetic content is a fetal genotype variant or a fetal haplotype variant. In one embodiment, the fetal genetic content is determined by inferring one or more maternal or paternal recombination locations and thereby determining a fetal genotype variant and a fetal haplotype variant. In another embodiment, the cell-free nucleic acid maternal sample can manifest a de novo variant of maternal origin or fetal origin.

Disclosed herein are methods for non-invasive determination of a cancer-associated mutation in a subject, comprising: obtaining a cellular sample from the subject comprising a set of chromosomes having genomic DNA and obtaining long germline haplotypes from the sample; obtaining a cell-free nucleic acid sample from the subject and determining the sequence of the cell-free nucleic acid sample; determining allele fractions of both tumor and normal alleles by analyzing the sequencing data from the cell-free nucleic acid sample; enumerating each allele from neighboring alleles; and inputting one or more enumerated alleles into a HMM to determine the presence of a cancer-associated mutation; and the long germline haplotypes are chromosome-spanning germline haplotypes, chromosome spanning germline haplotypes of -omes, or locus-spanning germline haplotypes.

Also disclosed herein are methods for non-invasive determination of genetic content in a sample from a transplantation recipient, comprising: obtaining a cellular sample from the transplantation recipient comprising a set of chromosomes having genomic DNA and obtaining long germline haplotypes from the sample; obtaining a cell-free nucleic acid sample from the transplantation recipient and determining the sequence of the cell-free nucleic acid sample; determining allele fractions of both donor and recipient alleles by analyzing the sequencing data from the cell-free nucleic acid sample; enumerating each allele from neighboring alleles; and inputting one or more enumerated alleles into a HMM to determine the genetic content of the sample; and wherein the long germline haplotypes are chromosome-spanning germline haplotypes, chromosome spanning germline haplotypes of -omes, or locus-spanning germline haplotypes.

BRIEF DESCRIPTION OF THE DRAWINGS

These and other features, aspects, and advantages of the present invention will become better understood with regard to the following description, appended claims and accompanying figures where:

FIG. 4 shows that HMM models on enumerated MPcfDNA data results in the determination of the fetal genetic content with >99% accuracy at fetal alleles where paternal alleles are homozygous to maternal transmitted alleles (MHet-PeqMT) in chromosome 1. FIG. 4A shows that the gHMM is more accurate than the bHMM (top), with a minimal loss of resolution (bottom), at 2× MPcfDNA. FIG. 4D shows the accuracy of a gHMM at various MPcfDNA sequencing depths, varying enumeration window sizes, at 0.99 posterior cutoffs (top) and corresponding loss of resolution (bottom). FIG. 4F shows that beyond 4× MPcfDNA sequencing depth, there is minimal loss of resolution from HMM and MPcfDNA read distribution (see FIG. 4E), with minimal gain in accuracy.

FIG. 5 Generalization of HMM models among different types of alleles for fetal determination. Determination of fetal genetic content is trivial in cases where both maternal and paternal alleles are homozygous. In cases where either maternal or paternal allele is heterozygous, or both are heterozygous, sophisticated mathematical models such as a hidden markov model (HMM) are necessary for accurate determination of fetal genetic sequence. More specifically, only maternal haplotypes are informative in maternal-only heterozygous alleles (MHet: Mat-Het, Pat-Hom), while only paternal haplotypes are informative in paternal-only heterozygous alleles (PHet: Mat-Hom, Pat-Het), and both haplotypes are informative in bi-parental heterozygous alleles (Bi-het: Mat-Het, Pat-Het). Therefore, in cases where both parents are heterozygous, a 4-state HMM may be needed to determine fetal genetic sequences. In each of these types, two conditions are manifested which in turn manifest unique expected allele fractions, with f defined as the fraction of fetal genetic content in MPcfDNA. In this figure example, specific configurations of HMM are modeled in each allele type. Other types of configurations may work equally well—for example, a 4-state single HMM for all types of alleles at once instance instead of multiple HMMs.

In FIG. 6B(ii), MHet HMM-based accuracy and post2 accuracy (posterior threshold 0) is depicted at various window sizes. Both HMM-based accuracy and post2 accuracy correlate well with likelihood (grey strip) and are maximized at a window size of 2-3 Mbs. When the window size is fixed to 2.5 Mb for MHet alleles, the standard deviation appears to minimally impact the HMM-based accuracy and post2 accuracy of the gHMM model (FIG. 6C).

FIG. 7 describes the combined results from different fetal allele types to determine the entire fetal genome (chromosome 1). A fetal chromosome consists of all three types of alleles, and therefore combining the results from each allele type allows an unbiased determination of the entire fetal genome. Here, HMM-based accuracy in each type (MHet, PHet, Bi-het) at posterior of 0.99 is described. Next, post-hmm window (PSW) correction is applied to eliminate or reduce micro switch errors manifested due to the HMM, to obtain post1 accuracy. Because of shared information between MHet and Bi-Het alleles, and between PHet and Bi-Het alleles, efforts to combine results from these two sets were performed to determine post2 Acm and Acp accuracies. During post2, further micro switches and conflicts between the predictions (between MHet and Bi-Het, and between PHet and Bi-Het) were resolved. The final accuracy (A=99.77%) and resolution (R=99.74%) is determined from Acm and Acp, and Rcm and Rcp. As mentioned above, predicting the entire chromosome 1 translates into predicting the entire fetal genome, as the fetus independently inherits each chromosome and by showing the disclosed method in chromosome 1, it can also be translated to other chromosomes and together the genome. The number of alleles predicted and resolved in each allele-type and combination steps is described, with a final accuracy and resolution of 99.7%. This clearly shows the precision of the disclosed methods in determining a fetal genome.

FIG. 8 shows that a HMM-based accurate (>98%) fetal exonic genetic content determination at 50× MPcfDNA exome, at all types of fetal alleles in chromosome 1. In FIG. 8B(i), likelihood of MHet (as in FIG. 6B(i)) is shown amongst different window sizes, and as expected, likelihood is a maximum at a window size of 2-4 Mbs, corresponding well with high accuracies in the same window range. The inset of FIG. 8B(i) demonstrates the linear relationship between accuracy and likelihood—the higher the likelihood, the higher the accuracy, as shown in FIG. 6B(i). In FIG. 8B(ii), MHet HMM-based accuracy and post2 accuracy (posterior threshold 0) are depicted at various window sizes. Both HMM-based accuracy and post2 accuracy correlate well with likelihood (grey strip) and are maximized at a window size of 2-4 Mbs. Altogether, the results for fetal exome determination follows similar principles and show similar accuracy as the case of fetal genome determination. These results are also applicable to other -omes such as a genome-wide collection of cis-regulatory elements or common variants, etc.

FIG. 9 describes the combined results from different fetal allele types to determine the entire fetal exome (chromosome 1). This figure follows the outline of FIG. 7. Because the exome represents 2-3% of the genome, only ~3,500 fetal alleles are to be determined in exonic chromosome 1, as opposed to 158,000 total fetal alleles (FIG. 7). As in the case of fetal genome determination (FIG. 6, FIG. 7), the exome determination is performed via HMM-based predictions, followed by post1-based micro-switch correction and finally by post2 micro-switch and conflict analyses. For simplicity, PSW (post-hmm window sizes for post1 and post2) is denoted in terms of number of alleles or SNVs. FIG. 9 clearly shows how the fetal exome can be determined at a final accuracy (A) of 99.12%; again showing the precision of the methods disclosed herein.

In FIG. 10(i), fetal exome predictions at PHet alleles are described. At these alleles only paternal haplotypes are informative and therefore fetal hidden state predictions are limited to P1 and P2. Several points can be noted from this analysis. First, the predictions are sparse (sparse black data points in P1 and P2 of figure), as the exome is only 2-3% of the genome. Second, the predictions agree very well with true recombination (vertical line). Third, errors primarily happen near the true recombinations, as expected. FIG. 10(ii) shows results from MHet alleles. Similar to PHet, only maternal haplotypes are informative in MHet, and therefore fetal base predictions are limited to M1 and M2. Unlike PHet, that had one true recombination event, MHet represents four recombinations between M1 and M2. This explains why MHet predictions generally had lower accuracy and resolution in comparison to PHet predictions (FIG. 6A, FIG. 8A, FIG. 7 and FIG. 9).

In FIG. 10(iii), results from Bi-het are shown. As before mentioned, at these alleles both parental haplotypes are informative and therefore fetal base predictions are based on 4 hidden states M1P1, M2P1, M1P2, M2P2 with 5 overall recombinations. The Bi-het case is often the most challenging type of allele because, a) it manifests 4 states, and b) the number of fetal alleles in Bi-het is fewer than the number of fetal alleles in MHet/PHet cases (FIG. 7 and FIG. 9). Together, FIG. 10 shows that a fetal exonic sequence can be precisely predicted in chromosome 1 by the methods disclosed herein and, by extension of the disclosed methods, to the entire exome as well as other -ome (*denotes centromere).

FIG. 12B shows a LSV deletion and FIG. 12C shows LSV duplication. Assuming the tumor and normal chromosomes are distributed as Poisson random variables, approximations from the central limit theorem were used to mathematically (shown in inset box equation) represent the required levels of cfDNA sequencing to confidently (99%) distinguish the allelic imbalances in a deletion LSV (−1) caused by the tumor (FIG. 12B). More specifically, $\varepsilon$=tumor fraction, Z=z-score with $\alpha$=0.99, and N is the cumulative coverage over LSV alleles. Longer haplotypes from, for example, HaploSeq enable minimal sequencing of cfDNA (FIG. 12B(i)), which is especially important in lower fractions of tumor in cfDNA (FIG. 12B(ii)). FIG. 12C shows similar results as for FIG. 12B, but for a duplication (+1) LSV.

DETAILED DESCRIPTION OF THE DISCLOSURE

Figure 1:
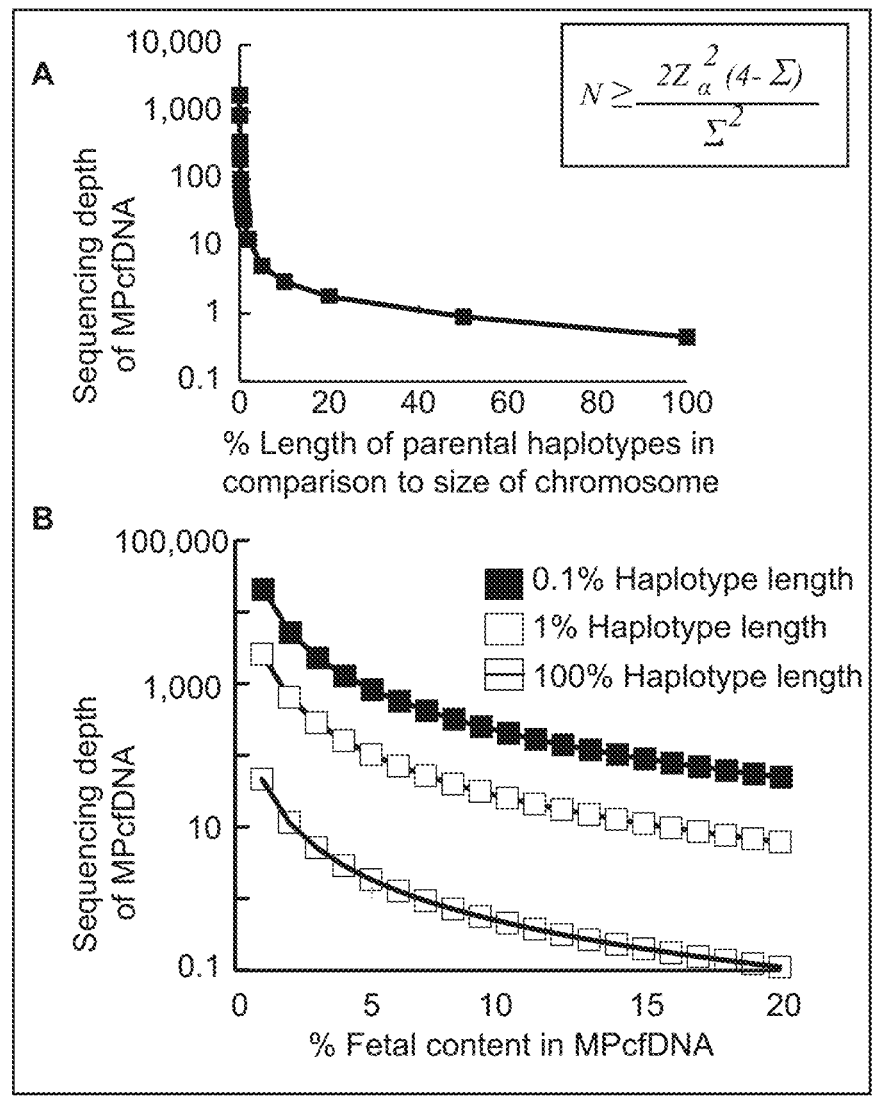
FIG. 1. Knowledge of long-range parental haplotype information reduces the amount of MPcfDNA sequencing required to distinguish maternal and fetal content, thereby enabling precise determination of fetal genetic content. Assuming the transmitted and the untransmitted parental haplotypes are Poisson random variables, approximations from the central limit theorem were used to mathematically (shown in inset box equation) represent the required levels of MPcfDNA sequencing to confidently (99%) distinguish the haplotypes. More specifically, $\varepsilon$=fetal fraction, Z=z-score with $\alpha$=0.99, and N is the cumulative coverage over maternally transmitted alleles where maternal is heterozygous and paternal is homozygous to the maternally transmitted allele. At these sites, the maternal haplotypes alone determine the fetal genetic content, as the paternal content is homozygous (FIG. 1A). When the maternal haplotype blocks are the length of the entire chromosome (100%), as achieved with HaploSeq, ~1× sequencing of the MPcfDNA is sufficient, assuming the presence of 10% fetal DNA in MPcfDNA (FIG. 1B). Similarly, three levels of maternal haplotype lengths, 0.1%, 1% and 100%, were modeled across different fetal fractions as determined by variable gestation times. With longer maternal haplotype knowledge, MPcfDNA sequencing required for distinguishing maternal and fetal content in MPcfDNA is quite low: 2-3× MPcfDNA sequencing at 5% fetal DNA.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

As used in this disclosure and the appended claims, the singular forms "a", "an" and "the" include a plural reference unless the context clearly dictates otherwise. As used in this disclosure and the appended claims, the term "or" can be singular or inclusive. For example, A or B, can be A and B.

Timely access to accurate genetic information can improve the understanding of human health and disease. Recently, next generation sequencing (NGS) methods have emerged as the standard method for obtaining an individual's genetic information. NGS methods are being used for disease diagnosis and monitoring. However, to truly enable precision medicine, some of the current challenges have to be solved. One challenge of NGS is in defining haplotypes. More specifically, humans inherit two copies of genetic material, maternal and paternal, and deconvoluting haplotypes of two copies has been very challenging. In other words, human genotypes, i.e. "parental merged" genetic information, can be obtained via current NGS, but unmerging the genotypes to discern haplotypes remain extremely difficult. Knowledge of haplotypes (along with genotypes) catalogues an individual's complete individual's genetic information, and is fundamental to the utility of genetics in precision medicine.

Another challenge of the current NGS approaches is to deconvolute genetic information from a mixed or impure sample. More specifically, while genetic information can be accessed from an individual's "pure" DNA source (for example, saliva, white-blood cells (WBCs) from blood, a tissue biopsy, etc.), deconvoluting mixture samples to determine genetic content is far more challenging. As a classic example of a mixture sample, maternal body fluid such as plasma contains cfNA (MPcfDNA) that contains genetic material from both the fetus and the mother, and determining the fetal genetic content from the MPcfDNA mixture enables detection of fetal genetic disorders. As fetal genetic defects including single-gene Mendelian disorders and aneuploidies are among the leading causes of miscarriages and congenital birth disorders, significant efforts have been made to deconvolute MPcfDNA to define fetal content.

Methods referred to as Non-invasive prenatal testing (NIPT) have enabled detection of fetal aneuploidies from MPcfDNA. But because the fraction of fetal content in MPcfDNA is small (~5-15%), and consists of DNA that is fragmented to 150 bp, determination of fetal genetic content (genotypes and haplotypes) to the level of SNVs remains challenging. Knowledge of SNV genotypes is fundamental for diagnosing single gene Mendelian disorders in the fetus. Further, non-invasive deconvolution of fetal haplotypes is necessary for assessing the risk for complex multi-genic disorders. Therefore, methods to define fetal genetic context in the context of SNV genotypes and haplotypes will have high clinical utility.

In the context of NIPT, a method, such as HaploSeq (as described above), can used to resolve the maternal and paternal haplotypes, and by leveraging long haplotypes, for example, chromosome-spanning (or locus-spanning) parental haplotypes, a novel hidden markov-based algorithm was developed by the inventors to determine fetal genetic content (genotypes and haplotypes) from minimal sequencing of MPcfDNA.

Prior to HaploSeq, obtaining long parental haplotypes was challenging. Several known methods (e.g. fosmid-based, dilution-based, 10× Genomics, Dovetail genomics, etc.) for obtaining haplotypes generates haplotypes of limited length (usually <1-5% of an average human chromosome of 100 Megabases), requiring excessive, time consuming, and costly deep sequencing of the MPcfDNA for an accurate fetal genetic inference. This is especially evident in early gestation when the fetal cfDNA can be as low as 3-5%—e.g. at 5% fetal cfDNA, as demonstrated in FIG. 1A and FIG. 1B.

Knowledge of long haplotypes, for example, chromosome-spanning parental haplotypes (100% of human chromosomes) can minimize the MPcfDNA sequencing depth required for accurate fetal genetic inference. However, known methods to generate parental chromosome-spanning haplotypes, such as chromosome-separation-based phasing or phasing via parent-child trios, are laborious to perform, require specialized equipment, and/or require genetic material from grandparents that are often unavailable.

HaploSeq is the only practical and scalable method for whole-genome (chromosome-spanning) and targeted haplotyping that can solve the problem of low chromosomal phasing, that is plaguing the earlier mentioned methods. HaploSeq is the first scalable, cost-effective method for assembling chromosome-spanning haplotypes, chromosome-spanning -ome haplotypes (exome or other -ome haplotypes), or targeted locus-spanning haplotypes in the absence of parental information, sperm samples, or specialized equipment.

This disclosure reveals a novel approach for deconvoluting a mixture sample. Exemplary types of mixture samples are, NIPT samples, oncology samples, and transplantation samples.

In summarizing for NIPT, the use of chromosome-spanning haplotypes of parents (obtained via HaploSeq) enables the determination of an entire fetal genome from low-depth (<10×) MPcfDNA sequencing. The knowledge of the chromosome-spanning parental haplotypes of -omes can enable determination of fetal -omes (exomes or other -omes, such as common variants sets or sets of cis-regulatory elements, etc.). In particular, an exome represents (2-3%) of the genome and is sparsely distributed throughout all chromosomes. Using Exome HaploSeq, information on long haplotypes, for example, chromosome-spanning parental exomes haplotypes is obtained and this information is used to determine a fetal exome from MPcfDNA. Using the same rationale, any specific fetal locus can be determined from MPcfDNA, with information regarding the corresponding parental haplotypes. Therefore, the methods disclosed herein demonstrate a true fetal sequencing assay from MPcfDNA or cfDNA from other body fluids that enables non-invasive determination of fetal genotypes and haplotypes in the context of SNV genotypes and haplotypes to determine an entire genome, exome (or other -ome), or any targeted locus, for timely and highly accurate diagnosis of a fetal genetic disorder.

A second example of deconvolution of a mixture sample can be found in the field of molecular oncology. Specifically, cfNA from a cancer patient's plasma, urine, or other body fluids (BF) comprises nucleic acids from normal cells as well as tumor cells. Therefore, efforts have begun to use cfDNA (which manifests cell-free tumor DNA (ctDNA)), as a means for the non-invasive detection of cancer-associated mutations or abnormalities. It is described herein, how knowledge of germline haplotypes (indicating normal genetic material) from an individual, allows for the accurate detection of cancer-associated mutations from using the data obtained from cfDNA sequencing. Depending on the size and location of the "to be inferred" cancer-associated mutation, as manifested in cfDNA, corresponding knowledge of germline haplotypes, allows for reduced sequencing of the cfDNA, saving time and money.

A third example of a mixture sample is cfNA from an organ transplantation recipient. Specifically, cfDNA from recipient plasma samples (RcfDNA) is known to comprise DNA originating from the recipient as well as the donor. Deconvoluting RcfDNA to quantify the amount of donor DNA in the recipient sample provides an indication of the transplantation outcome and allows for the monitoring of the transplantation procedure. Knowledge of recipient haplotypes can allow cost-effective measurements of donor genetic "contamination" from RcfDNA sequencing.

Together, the disclosure demonstrates that the knowledge of long haplotypes (parental, germline, etc.) facilitates cost-effective deconvolution of mixture samples to non-invasively determine a fetal genome, exome (or other -ome) or any targeted locus, or to non-invasively detect cancer-associated mutations, to non-invasively quantify donor contamination, along with other applications. Overall, the disclosed methods will allow the use of mixed-sample-based assays (e.g. cfDNA) to advance numerous clinical applications.

Ranges

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

About

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Haplotypes

As the human genome consists of two homologous sets of chromosomes, understanding the true genetic makeup of an individual requires delineation of the maternal and paternal copies, or haplotypes, of the genetic material. Haplotype reconstruction, also known as "haplotype phasing", is the act of delineating maternal and paternal haplotypes. A popular approach is to use of DNA or RNA sequencing data to group variant alleles that are inherited from the same parent. This grouping is called a haplotype block. See Browning et al. Am J Hum Genet 81, 1084-97 (2007). The utility of obtaining a haplotype in an individual can be several fold: first, haplotypes are useful clinically in predicting outcomes for donor-host matching in organ transplantation (Crawford et al., Annual Review Of Medicine 56, 303-320 (2005) and Petersdorf et al., PLoS Medicine 4, e8 (2007)) and are increasingly used as a means to detect disease associations (Studies et al., Nature 447, 655-660 (2007); Cirulli, et al., Nature Reviews. Genetics 11, 415-425 (2010); and Ng et al., Nature Genetics 42, 30-35 (2010)). Second, in genes that show compound heterozygosity, haplotypes provide information as to whether two deleterious variants are located on the same or different alleles, greatly impacting the prediction of whether inheritance of these variants are deleterious (Musone et al., Nature Genetics 40, 1062-1064 (2008); and Erythematosus, et al., Nature Genetics 40, 204-210 (2008); and Zschocke, Journal of Inherited Metabolic Disease 31, 599-618 (2008)). In complex genomes such as humans, compound heterozygosity may involve genetic or epigenetic variations at non-coding cis-regulatory sites located far from the genes they regulate (Sanyal et al., Nature 489, 109-113 (2012)), underscoring the importance of obtaining long haplotypes, for example, chromosome-spanning haplotypes. Third, haplotypes from groups of individuals have provided information on population structure (International HapMap, C. et al., Nature 449, 851-861 (2007); Genomes Project, C. et al., Nature 467, 1061-1073 (2010); and Genomes Project, C. et al., Nature 491, 56-65 (2012)), and the evolutionary history of the human race (Meyer et al., Science 338, 222-226 (2012)). Fourth, knowledge of haplotype structures is useful clinically for pre-natal non-invasive fetal sequencing (Kitzman, et al. Sci Transl Med 4, 137ra765 (2012)). Further, haplotypes are useful in understanding "allelic imbalances" in gene expression, DNA methylation, and protein-DNA interactions, which are known to influence disease susceptibility (Kong, A. et al. Nature 462, 868-1074 (2009), International Consortium for Systemic Lupus Erythematosus, G. et al. Genome-wide association scan in women with systemic lupus erythematosus identifies susceptibility variants in ITGAM, PXK, KIAA1542 and other loci. Nat Genet 40, 204-10 (2008), and Hindorff et al. Proc Natl Acad Sci USA 106, 9362-7 (2009)). Taken together, obtaining haplotype information is important for clinical and biomedical advances in human genetics. The contents of these references are incorporated by reference in their entireties.

A haplotype can be achieved via whole-genome sequencing (e.g. HaploSeq) and can span 100% of a chromosome (a chromosome-spanning haplotype), or any long portion of the chromosome (>0.05%, e.g. 0.1%, 1%, and so on). A long haplotype is defined as greater than about 0.05% of the total length of a chromosome up to 100% of the length of a chromosome.

A haplotype can be achieved via targeted sequencing of -ome (e.g. Exome HaploSeq) and can span the entire chromosome covering -ome elements (100% of the chromosome), or any long portion of the chromosome (>0.05%, e.g. 0.1%, 1%, and so on). For instance, Exome HaploSeq generates chromosome-span haplotypes covering only exonic alleles or chromosome-span haplotypes of exomes. A long haplotype is defined as greater than about 0.05% of the total length of a chromosome up to 100% of the length of a chromosome.

A haplotype can be achieved via targeted sequencing of a locus (e.g. targeted HaploSeq) and can span the entire locus (100% of the locus), or any long portion of the locus (>0.05%, e.g. 0.1%, 1%, and so on). A long haplotype is defined as greater than about 0.05% of the total length of a chromosome up to 100% of the length of a chromosome.

Enumeration

An enumeration is a complete, ordered listing of all the items in a collection. The term is commonly used in mathematics and computer science to refer to a listing of all of the elements of a set. In the context of the current disclosure, bases of the mixture cfDNA data, categorized by their allele-type, are enumerated and averaged together based on germline or parental haplotypes. More specifically, the allele fractions of a specific base from mixture cfDNA data is estimated by enumeration of cfDNA data from nearby bases on the same haplotype to cumulatively support a robust estimation of transmitted and untransmitted allele frequencies. The longer the haplotypes (for example, chromosome-spanning, or locus-spanning), the more alleles can be used for enumeration and therefore longer haplotypes maximizes the chances for robust estimations of allele fractions.

Deconvolution

Deconvolution is a process of resolving something into its constituent elements or removing complication in order to clarify it. In the context of the current disclosure, deconvolution of a mixture samples allows determining the genetic content of each constituent source. For example, deconvoluting MPcfDNA means determining the content of fetal and maternal genetic material.

Genome

A genome is any set of all genetic material including all chromosomal and non-chromosomal DNA from a genetic source. A genetic source may include, but is not limited to, eukaryotic, prokaryotic, cell-free, embryo, etc.

Nucleic Acid

A "nucleic acid" refers to a DNA molecule (e.g., a genomic DNA), an RNA molecule e.g., an mRNA), or a DNA or RNA analog. A DNA or RNA analog can be synthesized from nucleotide analogs. The nucleic acid molecule can be single-stranded or double-stranded DNA.

A Sample

A sample can comprise one or more cells or cell-free genetic material (cell free nucleic acids (cfNA) from an organism. A cell can be a diploid cell, an aneuploid cell, or a cancerous (tumor) cell. A sample can be obtained via a non-invasive (for example, a blood draw) or invasive (for example, surgery or a biopsy) method. A sample is termed a mixture sample or impure sample when it contains genetic material from distinct or different sources.

A sample can be a sample obtained from an organism (e.g., a patient) or from components (e.g., cells or cell-free nucleic acid sources) of an organism. The sample may be of any biological tissue, cell(s) or fluid. The sample may be derived from a subject, such as a human patient. Such samples include, but are not limited to, saliva, sputum, blood, blood cells (e.g., white cells), amniotic fluid, plasma, semen, bone marrow, and tissue, a fine needle biopsy sample, urine, peritoneal fluid, pleural fluid, hair, or cells therefrom. A sample may also include a section of tissue, for example, a frozen section taken for histological purposes. A sample may also include a substantially purified or isolated protein, membrane preparation, or cell culture.

Cell Free Nucleic Acids (cfNA)

Nucleic acids obtained from bodily fluids, where the nucleic acids (DNA, RNA, etc.) are "floating together" without a cellular architecture. RcfDNA is an example of a cell free nucleic acid.

An "-OME"

In this disclosure, an -ome is a term used to refer collection of elements of the same type that are distributed throughout a chromosome and genome. For example, an exome is a collection of exons. A cis-regulatory -ome is a collection of cis-regulatory elements present in the genome.

Hidden Markov Model (HMM)

The term HMM and HMM-based are used interchangeably throughout the disclosure to mean the use of any type of HMM.

The Hidden Markov Model (HMM) is a popular statistical tool for modeling a wide range of time series data. Hidden Markov models (HMMs) are a formal foundation for making probabilistic models of linear sequence 'labeling' problems. They provide a conceptual toolkit for building complex models just by drawing an intuitive picture. They are at the heart of a diverse range of programs, including gene finding, profile searches, multiple sequence alignment and regulatory site identification. HMMs are the Legos of computational sequence analysis (as described in Eddy, S. R., Nature Biotechnology 22, 1315-1316 (2004). The contents of this reference are incorporated by reference in its entirety.

Hidden Markov Model are also described in Browning et al., Nature Reviews Genetics 12, 703-714 October 2011, US Publication No. 2014/0045705, and US Publication No. 2013/0316915. The contents of these references are incorporated by reference in their entireties.

A HMM can be a 2-state or a 4-state or generally multi-state model comprises of one or many Hidden-Markov Models per allele-type -one or many models for maternal-only heterozygous alleles, one or many models for paternal-only heterozygous alleles, and one or many models for bi-parental heterozygous alleles, wherein the distribution of observations can be modeled via binomial, multinomial, a single or a mixture Gaussian, or other mathematical distributions, followed by one or many consensus algorithms for making the best possible fetal genetic content determination.

A HMM can be a single or multi instance 2-state, 4-state or generally multi-state model consistent across all the allele-types, wherein the distribution of observations can be modeled via binomial, multinomial, a single or a mixture Gaussian, or other mathematical distributions, followed by one or many consensus algorithms for making the best possible fetal genetic content determination.

More generally, a HMM can be a single instance or multi instance multi-state HMM model, where the distribution of observations can be modeled via binomial, multinomial, a single or a mixture Gaussian, or other mathematical distributions.

A HMM model can take the enumerated allele fractions as input and predicts the state of a mixture sample, including examples in NIPT, oncology and transplantation or other examples.

Post-HMM Analyses

Post-HMM analyses can be performed either independently for each allele-type or via a combination analyses, or both. A post-HMM analysis helps to reduce errors from micro-switches, errors from conflicting predictions among allele-types, or other types of errors. A post-HMM analysis improves the accuracy and the resolution of the deconvolution analyses.

Variants

The methods disclosed herein can be used to determine any type of genetic variant. A variant can be a single nucleotide variant (SNV), an indel, a structural variant, an insertion, a deletion, duplication, an inversion, or a translocation.

Genotype Variant

Haplotype-unresolved or parental-unmerged list of variants that make up the genetic content of a cell, cell-free material or an organism.

Haplotype Variant

Haplotype-resolved list of variants that make up the genetic content of a cell, cell-free material or an organism. Haplotypes are relevant in a diploid (e.g. humans) and polyploidy organisms (e.g. some varieties of bread wheat have 6 copies of each chromosome).

A De Novo Variant

De novo variants are non-inherited variants. Inherited and de-novo variants together make up the genetic content of a cell, cell-free material or an organism. In the context of NIPT, the de novo variants of type megabase-scale structural variations of fetal or maternal origin can be determined by deviations from expected read counts from the region of de novo copy number variation manifested in sequencing data from maternal cell-free nucleic acid sample. Other types of de novo variants such as SNVs require deep sequencing (>50×) of maternal cell-free nucleic acid sample.

Allele-Types

In the context of NIPT, fetal genetic determination is performed primarily on MHet (maternal only heterozygous alleles), PHet (paternal only heterozygous alleles), Bi-Het (both parents heterozygous alleles). Other allele-types such as Bi-HomEq (both parents homozygous to same allele) and Bi-HomUn (both parents homozygous to different alleles) are trivially determined. In the context of oncology and transplantation, both homozygous and heterozygous alleles in germline and or mixture cfDNA is useful for mixture deconvolution.

Neighboring Fetal Alleles

Neighboring fetal alleles are used in enumeration. Specifically, enumeration is performed for each fetal allele from neighboring fetal alleles of the same allele-type on the same parental haplotypes, wherein a "neighborhood" is defined as a region of size 100 Kilobases to 20 Megabases.

Sequencing

Any suitable sequencing platform or technology can be used for sequencing in the disclosed methods. For example, any next generation sequencing method, massively parallel sequencing platform, cyclic-array method, sequencing by hybridization, nanopore sequencing, real-time observation of DNA synthesis, sequencing by electron microscopy, shotgun sequencing, re-sequencing, de novo assembly, exome sequencing, targeted locus sequencing (e.g. MHC), targeted -ome sequencing (e.g. exome sequencing, cis-regulatory elements sequencing, etc.), DNA-Seq, Targeted DNA-Seq, Methyl-Seq, Targeted methyl-Seq, DNase-Seq, Sano-Seq, FAIRE-seq, MAINE-Seq, RNA-Seq, ChIP-Seq, RIP-Seq, CLIP-Seq, HITS-Seq, FRT-Seq, NET-Seq, Hi-C, Chia-PET, Ribo-Seq, TRAP, PARS, synthetic saturation mutagenesis, Immuno-Seq, Deep protein mutagenesis, PhIT-Seq, SMRT, or genome-wide chromatin interaction mapping or other methods not mentioned here can be used in the disclosed methods.

Sequencing Depth

Sequencing depth defines the number of times a genetic base is sequenced.

Accuracy of Genetic Content

Using the disclosed methods, the genetic content of a mixture sample can be determined at an accuracy rate of about 85% to 90%, 90% to 95%, 95% to 96%, 96% to 97%, 97% to 98%, 98% to 99%, or 99% to 100%.

Enumeration Window Size

Any of the disclosed methods can have a window size from about 100 Kilobases to about 20 Megabases.

The Principle of Haplotype-Based Enumeration

As sequencing technology becomes cheaper and more efficient, many efforts are now shifting to provide a higher level of genetic data interpretation to advance precision and personalized medicine. While efforts have focused on genetic sequencing and interpretation of pure samples (e.g. DNA from an individual), an important step in precision medicine is to deconvolute a sample that contains genetic data originating from different sources (a "mixture" or an "impure" sample). Several examples of such mixture samples exist in nature. For example, maternal plasma from pregnant women contains cell-free nucleic acids (MPcfDNA) that manifests DNA from the mom as well as the fetus (5-15% fetal fraction in MPcfDNA). Deconvoluting MPcfDNA to determine fetal genetic content is key for the purpose of non-invasive prenatal testing (NIPT). Current methods can determine fetal aneuploidies and large fetal copy-number variation from MPcfDNA, but determining fetal genetic content to the level of single nucleotide variation (SNVs) has been challenging. Genotypes and haplotypes of fetal SNVs inform Mendelian and other complex genetic inherited diseases that cause genetic defects in >1% of births, and therefore it is important to non-invasively determine genotypes and haplotypes of fetal SNVs.

Recognizing the importance of determining a fetal sequence to the level of SNV genotypes and haplotypes, several research groups have attempted to use parental haplotypes to determine fetal genetic content from MPcfDNA. Specifically, these studies have revealed that parental haplotypes, when phased over long distances, facilitate distinguishing of the transmitted parental haplotypes to the fetus, from the untransmitted parental haplotypes (FIG. 1A), especially at gestation times when a fetal fraction in MPcfDNA is even lower (e.g. 5% in FIG. 1B). This process allows for the accurate inference of a fetal genotype, subsequently the fetal haplotypes can be inferred in the context of parental and fetal genotypes (parent:child trio analyses). Due to the difficulty in obtaining long parental haplotypes (for example, chromosome-spanning haplotypes), current methods require costly excessively deep sequencing of MPcfDNA (depth >40×). More specifically, these methods predict fetal genotypes from information contained only on the current MPcfDNA base to be predicted, and thereby requiring deep sequencing of every base of MPcfDNA (depth >40×) to obtain a robust estimate of transmitted and untransmitted allele frequencies. Deep sequencing is expensive and also results in errors in the range of 1-5% in fetal genotype determination. The cost-prohibitive nature and the inaccuracies impair the use of NIPT in clinical applications.

Previously, the HaploSeq method was invented HaploSeq (as described in S. Selvaraj, et al., Nature Biotechnology, "Whole genome haplotype reconstruction using proximity-ligation and shotgun sequencing", published online 3 Nov. 2013, doi:10.1038/nbt.2728; Selvaraj, et al. BMC Genomics, "Complete haplotype phasing of the MHC and KIR loci with targeted HaploSeq", published online 5 Nov. 2015, doi: 10.1186/s12864-015-1949-7; US Publication No. 2016/0160275 entitled "Whole-genome and targeted haplotype reconstruction"; and U.S. Provisional Patent Application (Application No. 62/234,329, filed Sep. 29, 2015) entitled "Whole-exome haplotype reconstruction"), to determine chromosome-spanning haplotypes and targeted haplotypes from an individual's cells (e.g. from white blood cells (WBC) in blood). Disclosed herein is the use of HaploSeq to generate complete and chromosome-spanning parental haplotypes (FIG. 2A, and FIG. 2B(i)). Using HaploSeq in combination with an innovative fetal inference algorithm, results in the determination of a fetal genotype or haplotype using minimal sequencing of MPcfDNA. A process known as "enumeration" accomplishes this. More specifically, differing from the current paradigm in which fetal genotypes is predicted from information contained only on the "to be predicted" MPcfDNA base, the novel approach described herein enumerates MPcfDNA data from nearby bases on the same haplotype to cumulatively support a robust estimation of transmitted and untransmitted allele frequencies. Such an enumeration enables low-variance estimates of allele frequencies from lower sequencing of MPcfDNA. Described herein are examples of how enumeration has allowed for the reduction of sequencing depth of MPcfDNA from 40-70× depths required in current methods to <10× to determine the entire fetal genome (genotypes and haplotypes). The enumerated allele frequencies, described below, when inputted into an HMM, can determine a fetal genome with an error rate of <0.5% (illustrated in FIG. 7), in comparison to current methods with an error rate of 1-5%, even with a >40× MPcfDNA depth. It is key to the disclosure to understand that enumeration is maximized with the knowledge and use of longer parental haplotypes. Thus, chromosome-spanning parental haplotypes obtained from HaploSeq are critical for maximum enumeration and minimized MPcfDNA sequencing.

Thus, haplotype enumeration allows for cost-effective and accurate deconvolution of fetal genetic content from a mixture MPcfDNA sample. While MPcfDNA is one example of a mixture sample, many other examples exist, including, but not limited to oncology samples and transplantation samples. For instance, cfDNA from a cancer patient contains DNA from normal cells as well as tumor cells, and thus knowledge of long germline (normal) haplotypes allows for the maximum enumeration of cfDNA, resulting in the determination of cancer-associated mutations using minimal sequencing of cfDNA. In a similar example, cfDNA from a transplantation recipient (RcfDNA) contains DNA from the recipient as well as from the donor. Knowledge of long recipient (normal) haplotypes allows for the maximum enumeration of RcfDNA to quantify the amount of donor DNA using minimal sequencing of RcfDNA.

In summary, this disclosure addresses the aforementioned unmet need by providing a method for cost-effective deconvolution of a mixture sample, such as cfDNA, across several clinical settings including, a) deconvolution of the mixture MPcfDNA sample to non-invasively determine the entire fetal genome (genotypes and haplotypes) by leveraging parental long haplotypes, for example, chromosome-spanning haplotypes in combination with low-depth (<10×) MPcfDNA sequencing, b) deconvolution of the mixture MPcfDNA to non-invasively determine the fetal -ome sequence (exomes or other -omes such as common variants sets or sets of cis-regulatory elements, condition-specific gene panels, etc.) by leveraging parental long haplotypes, for example, chromosome-spanning haplotypes of -omes in combination with minimal sequencing of MPcfDNA -ome, c) deconvolution of the mixture MPcfDNA to non-invasively determine a user-defined target fetal locus sequence by leveraging parental haplotypes of corresponding locus in combination with sequencing of MPcfDNA representing the target locus where the sequencing depth depends on the length of the locus, d) deconvolution of the mixture cfDNA to detect tumor-associated mutations by leveraging germline haplotypes in combination with cfDNA sequencing for cancer detection, monitoring and surveillance, and e) deconvolution of the mixture recipient cfDNA (RcfDNA) by leveraging recipient haplotypes in combination with RcfDNA sequencing to quantify donor contamination to understand transplantation outcome, and/or monitoring, and (f) other utilities.

Absence of Enumeration Leads to Deeper Sequencing in NIPT

Other researchers have proposed methods similar to enumeration. For instance, in the case of NIPT, Dennis Lo and colleagues proposed "haplotype dosage". This method engages in finding relative representations of parental haplotypes to infer transmitted versus untransmitted haplotypes. More specifically, this method classifies a parental chromosome as "type alpha" segments and "type beta" segments, where the fetus is homozygous versus heterozygous respectively, in maternal heterozygous and paternal homozygous sites. Then, for each segment they determine which maternal haplotype got transmitted to the fetus using the principle of dosage or over-representation of haplotypes. Because of arbitrary segmentation, the parental haplotypes are not fully utilized in this method and such a method, in spite of deep MPcfDNA sequencing, results in reduced accuracy when compared to better formulated statistical models of fetal inference, such as Hidden Markov models (HMMs), as demonstrated by Jay Shendure and colleagues. However, owing to incomplete parental haplotypes via fosmid methods used by Jay Shendure and colleagues, an enumeration-based HMM approach is not feasible, because of frequent haplotype switch errors (haplotype error every ~300 Kb, resulting in phasing of <1% of an average human chromosome on a contiguous haplotype). Switch errors create fake recombination junctions and thereby complicate enumeration as well as fetal inference procedures. Despite having chromosome-spanning haplotypes, generated from expensive and impractical grandparental sequencing, the multinomial algorithm proposed by researchers at Beijing Genome Institute (BGI) did not include enumeration, and therefore did not effectively utilize the parental information, resulting in the requirement of a high MPcfDNA sequencing depth (40×-50×) for fetal inference with up to a 5% error. All of the methods described above are expensive, due to the requirement of high-depth MPcfDNA sequencing for fetal genetic sequence inference.

EXAMPLES

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example 1: Impact of Maximal Enumeration Via HaploSeq in the Context of NIPT

The methods described herein fully utilize HaploSeq-based chromosome-spanning parental haplotypes via long-range and maximal enumeration, therefore, facilitating minimal and low-depth MPcfDNA sequencing. This innovative approach supports the theoretical limit estimations shown in FIG. 1A, that long parental haplotypes drastically reduce the required sequencing depth of MPcfDNA for the determination of a fetal genome (FIG. 2B (i)). Further, the feasibility of chromosome-spanning -ome (e.g. exome) parental haplotypes via HaploSeq means a fetal -ome (e.g. exome) can be determined from -ome targeted sequencing of MPcfDNA (FIG. 2B (ii))—the key is -ome elements are distributed across the entire chromosome and thus, chromosome-spanning haplotypes of parental -omes enables maximal enumeration and minimal MPcfDNA -ome sequencing. In addition, any targeted fetal locus can be determined with the knowledge of parental haplotypes of that locus, and by targeted sequencing of that locus from MPcfDNA. For example, a fetal MHC locus (4 Mb region) can be determined with the knowledge of parental locus-spanning MHC haplotypes along with MHC targeted sequencing of MPcfDNA (FIG. 2B (iii))). A key point to note is that the MHC parental haplotypes need to span the entire MHC locus, so that maximal enumeration would be possible (enumeration from all possible bases from the locus), thereby reducing the amount of MHC-MPcfDNA sequencing required.

Figure 3A:
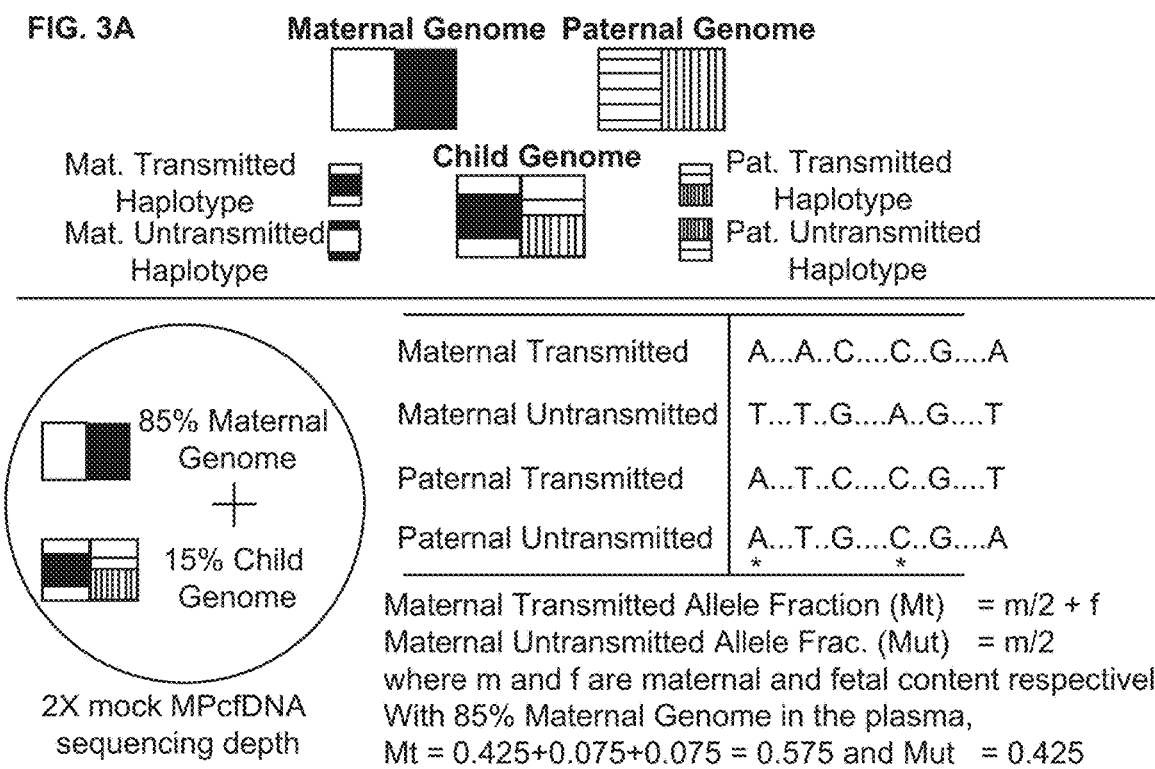
FIG. 3 shows fetal genetic content determination from enumerated MPcfDNA sequencing FIG. 3A show the experimental design of a "mock" MPcfDNA sequencing. The transmitted maternal and paternal haplotypes together manifest the fetal genetic content and for simplicity, only the fetal alleles where paternal alleles are homozygous to maternal transmitted allele are analyzed (MHet-PeqMT, grey bases). At these alleles, maternal haplotypes alone determine the fetal content, with the transmitted and the untransmitted alleles having fractions 0.575 and 0.425 respectively, assuming a 15% fetal fraction in MPcfDNA (FIG. 3A). Even at 2× MPcfDNA sequencing, the transmitted and untransmitted haplotypes can be distinguished (FIG. 3B). In analyzing MPcfDNA from chromosome 1, the raw data, used by current algorithms, does not follow the expected fractions (bottom, dashed horizontal lines around 0.575 and 0.425), owing to the low 2× depth of MPcfDNA sequencing. By enumerating on M1 and M2 haplotypes over a length of 5 Mbs (top), precise recombination locations were discerned (#, grey vertical strip) that agrees with true recombination (black dashed vertical lines) (*denotes centromere) (FIG. 3C).
Figure 3B:
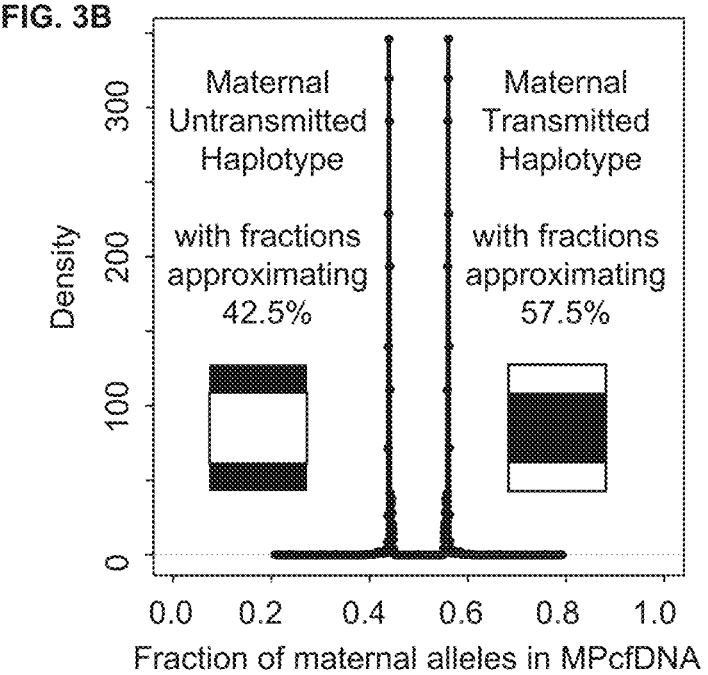

To show the impact of the disclosed enumeration method, the following experiment was designed. A haplotyped parent-child trio from the 1000 Genomes Project (Paternal: GM12877, Maternal: GM12878, Child: GM12879) was leveraged, and publicly available genome-sequencing datasets (fastq format) were downloaded. The maternal and child genome sequence files were mixed in the ratio of ~15:85 to mimic MPcfDNA, and this "mock-MPcfDNA" was analyzed at a low-depth 2× sequencing depth (FIG. 3A). This approach determines fetal genotype and haplotype concurrently: the fetal determination problem was formulated the following way. If maternal haplotypes are defined as M1 and M2, and paternal haplotypes as P1 and P2, there are four possible parental transmissions (M1P1, M1P2, M2P1, M2P2) at each base position in the fetal genetic sequence. Therefore, the fetal haplotype can be determined by precisely identifying the locations of parental recombination events, enabling exact inference of parental transmissions. Because of this insight, it is believed that low-depth MPcfDNA sequencing would enable detection of recombination events if two conditions are true: (1) transmitted versus untransmitted parental haplotypes can be distinguished at low-depth MPcfDNA sequencing, and (2) MPcfDNA sequence data from nearby bases on the same parental haplotype can be enumerated to compensate for low-depth MPcfDNA sequencing to estimate robust allele fractions for predicting a fetal base. Indeed, the analysis presented herein demonstrates that transmitted and untransmitted maternal haplotypes can be readily distinguished in mock-MPcfDNA (FIG. 3B), fulfilling condition 1.

As previously mentioned, the second condition represents a key departure from the current NIPT paradigm, wherein determining the fetal genotype at a given position relies solely on the MPcfDNA sequencing data at that position (hence their need for high-depth sequencing of 40-70×). Instead, in the disclosed methods, the MPcfDNA sequencing data is enumerated across the known parental haplotypes to obtain low-variance and robust allele frequencies. These allele frequencies are considered as "observed" values in a Hidden Markov model (HMM) to predict the hidden fetal base (state) at a given position. Specifically, the base predictions are achieved by predicting the fetal base at a given position by employing a HMM where the base is the hidden haplotype "state" and the state could be a 2-state (M1, M2 or P1, P2) or 4 states: M1P1, M2P1, M1P2, M2P2. For this model to work, both the relative rarity of recombination events (~1/chromosome arm) and the availability of parental haplotypes from HaploSeq (for enumeration) are used. As an example, to predict fetal bases from sites that are maternal-only heterozygous, where paternal allele is homozygous to the maternally transmitted allele (MHet-PeqMT), only the maternal haplotype is informative. Therefore, these fetal bases can be predicted via a 2-state HMM model where the states are M1 (Maternal Haplotype 1), M2 (Maternal Haplotype 2). In particular, to predict the fetal state of a specific MHet-PeqMT site, allele fractions from other MHet-PeqMT sites within a window (e.g. 5 Mb upstream and downstream of the base of interest) are enumerated in order to gather a cumulative and robust allele fraction input to the HMM. Because MHet-PeqMT alleles are distributed among the entire chromosome, chromosome-spanning parental haplotypes from HaploSeq would allow enumerating from distal and consequently more MHet-PeqMT alleles and thereby generate robust allele fractions even at minimal MPcfDNA sequencing. In other words, robust enumeration is enabled only because HaploSeq generates long haplotypes >5 Mb and the probability of a recombination event within that 5 Mb window is low. Indeed, the experiments described herein show that the enumeration approach fulfills condition 2 (FIG. 3C, upper panel), compensating for noise in the low-depth 2× mock-MPcfDNA sequencing data and identifying precise locations of recombination, which cannot be located using non-enumerated low-depth raw allele fractions (FIG. 3C, lower panel). In other words, use of non-enumerated raw allele fractions needs deep MPcfDNA sequencing of 40-70× to observe the expected fractions of 0.575 and 0.425 (assuming 15% fetal fractions) for transmitted and untransmitted alleles respectively, and low-depth MPcfDNA sequencing ~2× sequencing depth for example generates a very noisy pattern (FIG. 3C, lower panel). By innovatively enumerating over parental haplotypes over large window sizes, sufficient insight is gained into the parental recombination patterns to precisely infer fetal genetic content (FIG. 3C, upper panel). Using this approach, the predicted recombination sites (light vertical strips) closely align to the true recombination sites (black dotted lines).

Example 2: A HMM with Enumerated Input from Low-Depth Sequencing of MPcfDNA Accurately Determines a Fetal Sequence With the enumerated allele fractions as observed values, one aspect of the disclosure is the use of a HMM algorithm that assumes that the hidden haplotype state of the fetus (2-states: M1, M2) truly emits the enumerated observations of allele fractions via a binomial distribution in MHet-PeqMT alleles. A 2-state binomial HMM model determined fetal genetic content with >98% of accuracy (FIG. 4A) with 5 Mb enumeration, at 2× mock-MPcfDNA sequencing. This is remarkable as the method achieved an accuracy equivalent to other methods that used >40× MPcfDNA sequencing, but at 2× MPcfDNA sequencing, therefore reducing the sequencing cost by over 20-fold. While a binomial-HMM algorithm is a natural choice, as it directly models the probability of hidden state emitting the enumerated observation via a binomial expectation (p(success)=0.575 in the example), it could be deficient in handling the standard errors originating from the enumeration process, which is evident in the similar estimates of accuracy across varying stringencies of posterior probability in the HMM prediction (FIG. 4A). Consequently, it was reasonable to assume that a model that predicts the probability of hidden fetal state emitting the enumerated observation via a Gaussian approximation might be able to overcome the deficiency in handling of the standard errors. The Gaussian approximation increased the accuracy to >99% at higher posterior stringencies (FIG. 4A). Notably, increasing the stringency of the posterior results in a small loss in resolution (LOR, the fraction of variants unpredicted) of the fetal sequence determination (FIG. 4A, bottom panel) because higher posterior stringent models are skeptical of the fetal haplotype prediction at alleles near the true recombination junction. Nonetheless, a small sacrifice in resolution is offset by significant gains in accuracy, especially with such low-depth sequencing data.

Example 3: Optimizing of Enumeration Window Size

Figure 4B:
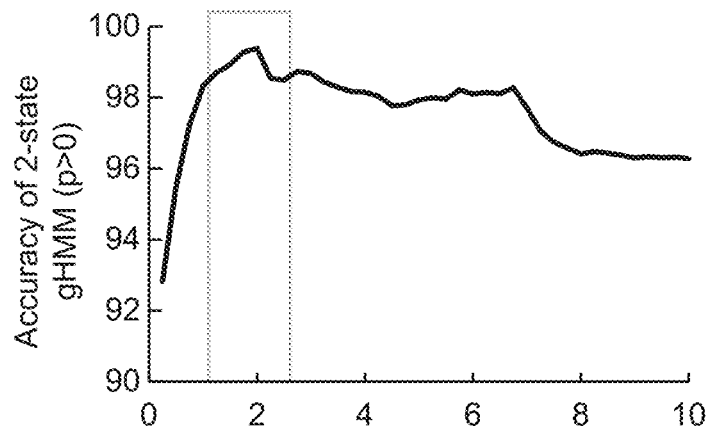
FIG. 4B shows the accuracy of gHMM across multiple enumeration window sizes, with a window size of ~2 Mbs performing best at 2× sequencing of MPcfDNA.
Figure 4C:
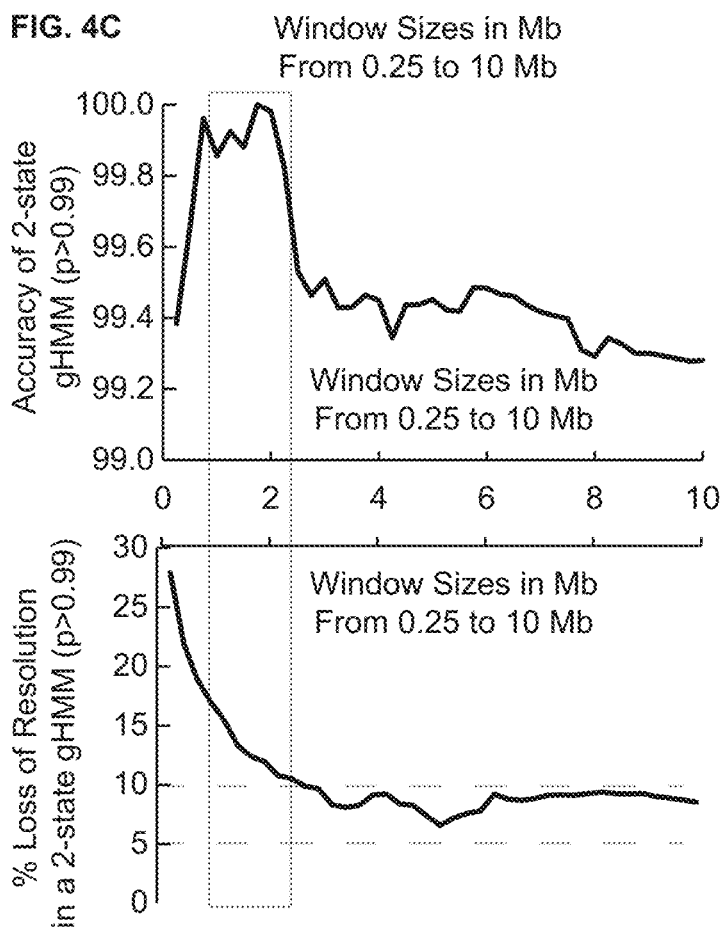
FIG. 4C is the same as FIG. 4B, but with a posterior threshold of 0.99. The accuracy reaches 99.9-100% around 2 Mbs window size, with a nominal loss of resolution (grey strip).

An important feature of the disclosure is the correct parental haplotype enumeration block window. A 5 Mb sliding window provides a robust input for the 2-state Gaussian HMM to predict the fetal genotype and haplotypes with >99% accuracy in our mock-MPcfDNA data at MHet-PeqMT alleles sequenced at 2× (FIG. 4A). A longer enumeration window size could enable a more powerful cumulative input to the HMM, but the probability of recombination in that window is also higher. At the same time, shorter window sizes may not have enough data points to result in a powerful HMM input. Therefore, to resolve such a trade-off, multiple window sizes were analyzed in order to leverage the best possible HMM input to obtain the highest accuracy of fetal sequence inferences. Our analyses of MHet-PeqMT alleles revealed that enumerating over ~2 Mb window sizes, both upstream and downstream, of every MHet-PeqMT allele generates the best accuracy (~99.5%) for chromosome 1 (FIG. 4B). With higher posterior stringency of p>0.99, the accuracy reached 99.8-100% with ~10% LOR (FIG. 4C). In other words, while 99.5% accuracy is feasible with no LOR, >99.8% becomes a possibility with 10% LOR (FIG. 4B and FIG. 4C). Regardless, these results show that 2× MPcfDNA sequencing is largely sufficient to determine a fetal genotype and haplotype, given the knowledge of the parental haplotypes.

Example 4: Optimization of MPcfDNA Sequencing Depth

Figure 4E:
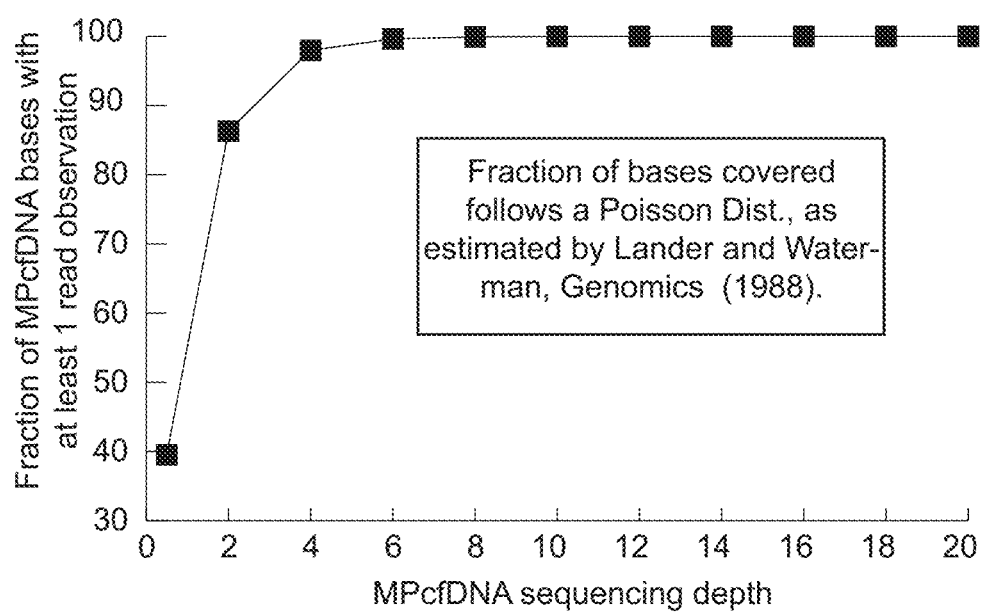
FIG. 4E shows that as the HMM predicts fetal genetic content only at bases observed in the simulation, there is an inherent loss of resolution due to the Poisson distribution of MPcfDNA sequencing reads. Together, these two sources (HMM and MPcfDNA read distribution) contribute to loss of resolution.

Another aspect of the disclosure is the MPcfDNA sequencing depth. The methods disclosed herein generate a highly accurate determination of fetal genetic content at 2× MPcfDNA sequencing. However the 10% LOR can be improved resulting in a more comprehensive fetal sequencing. One way to reduce the 10% of LOR is deeper sequencing of MPcfDNA. Therefore, the performance (accuracy and LOR) of our approach in MHet-PeqMT alleles was analyzed at various MPcfDNA sequencing depths (FIG. 4D). Three points emerge from this analysis. First, for this example, ~2 Mbs seems to be the optimal window size regardless of the MPcfDNA sequencing depth. However, the number of recombination events in chromosome 1 (used in this example) is 4, and the number of recombination events in an average human chromosome of length 100 Megabases is generally 1 or 2, so it is possible that a different window size would generate an optimal result for another chromosome. A skill of the art can enable estimation of the optimal window size for any given chromosome, as shown here for chromosome 1. Second, beyond 4× MPcfDNA sequencing, the accuracy is ~99.9-100% with a 2% LOR at a posterior cutoff of 0.99. Third, in this example both the accuracy and LOR seems to have reached a "saturation" point and therefore deeper sequencing beyond 4× may not add significant value for fetal inference. In addition, due to the Poisson distribution of sequencing read data, the fraction of bases with at least one sequencing read covering it, reaches ~100% at 4× sequencing (FIG. 4E). This means at 2× MPcfDNA sequencing, the total LOR is ~35% (10% from HMM, p>0.99 and 15% from MPcfDNA read distribution), while at 4× the total LOR is 2-3% (as MPcfDNA read distribution is 0% LOR). In summary, in this example, 4× MPcfDNA sequencing generated a more comprehensive and accurate fetal sequence determination when compared to 2×, and deeper MPcfDNA sequencing (>4×) may or may not add any significant value in fetal inferences (FIG. 4F). The determination of 4× MPcfDNA sequencing being sufficient was tested only in MHet-PeqMT alleles, and other allele-types might need a higher depth of MPcfDNA sequencing, as could also be the case with samples comprising a lower fetal fraction in the MPcfDNA.

Example 5: Generalizing the Disclosed Methods: From MHet-PeqMT to all Types of Fetal Alleles It should be noted that the results discussed above are based on analyses focused on MHet-PeqMT alleles (type 1 and condition 1 as defined in FIG. 5) and is based on mock-MPcfDNA containing 15% fetal fraction. To generalize these results, we performed enumeration and HMM analyses in all types (and conditions) of alleles. It should be noted that not all fetal bases need to be inferred—fetal bases that are the same as the parents are trivially inferred and so are fetal bases where both parental alleles are homozygous (Bi-hom: Mat Hom., Pat Hom.). Sophisticated mathematical models are required only for fetal alleles that are heterozygous at least in one parent. Therefore, the possible type of alleles were divided up as MHet, PHet, and Bi-Het, and designed specific HMM algorithms for each type (FIG. 5). In the case of MHet, only maternal haplotypes (M1,M2) are informative and because MHet had two conditions, two 2-state HMMs were designed. Specifically, at every MHet fetal base to be inferred, enumeration was performed independently over alleles that can occur as in condition 1 and condition 2 (FIG. 5), where conditions were defined assuming M1 as the transmitted haplotype. If M2 was the transmitted haplotype, the nature of the conditions switches—and the HMM was designed to precisely capture these switches, thereby defining recombination junctions. A 2-state HMM model was used for each condition and the fetal hidden state (M1, M2) was inferred using the maximum likelihood between these two HMM models (that represent two conditions) to determine the fetal haplotype and genotype. As mentioned above, the enumeration depends on the length of the parental haplotypes and because HaploSeq generates chromosome-spanning haplotypes, this approach maximally utilizes the benefits of enumeration. In addition, chromosome-spanning haplotypes by definition result in the absence of switch errors thereby simplifying the fetal determination process. In other words, other haplotyping methods that utilize fosmids, 10× genomics or Dovetail genomics, generate switch errors every 300 Kb-2 Mb that create fake recombination junctions, which in turn complicates enumeration and the HMM model. For PHet, a similar strategy of two 2-state HMMs was used, and here only the paternal haplotypes were informative and therefore the hidden states were P1, P2. In the case of Bi-Het, both parental haplotypes are informative and therefore, a single 4-state HMM truly captures the essence of these alleles.

Because a chromosome contains three types of alleles (MHet, PHet, Bi-Hets), in one embodiment of the disclosure, post-HMM steps are used to improve the accuracy of fetal determination in a model with a HMM configuration per allele type. In one step, micro-switches (post1) manifested from incorrect HMM predictions were corrected for, and this was conducted in each allele type independent of other allele types. In another step, the shared results between MHet and Bi-het were analyzed, and the shared results between PHet and Bi-het were also analyzed, to further correct micro-switches and resolve any conflicts in maternal and paternal predictions of fetal states (post2), respectively. These results are summarized in FIG. 6. Specifically, we show the results from these analyses at 6× mock-MPcfDNA sequencing from chromosome 1 (FIG. 6A) among all three allele types. More specifically, each of the three cases achieved >99% post2 accuracies with minimal LOR at a 2-3

Figure 6A:
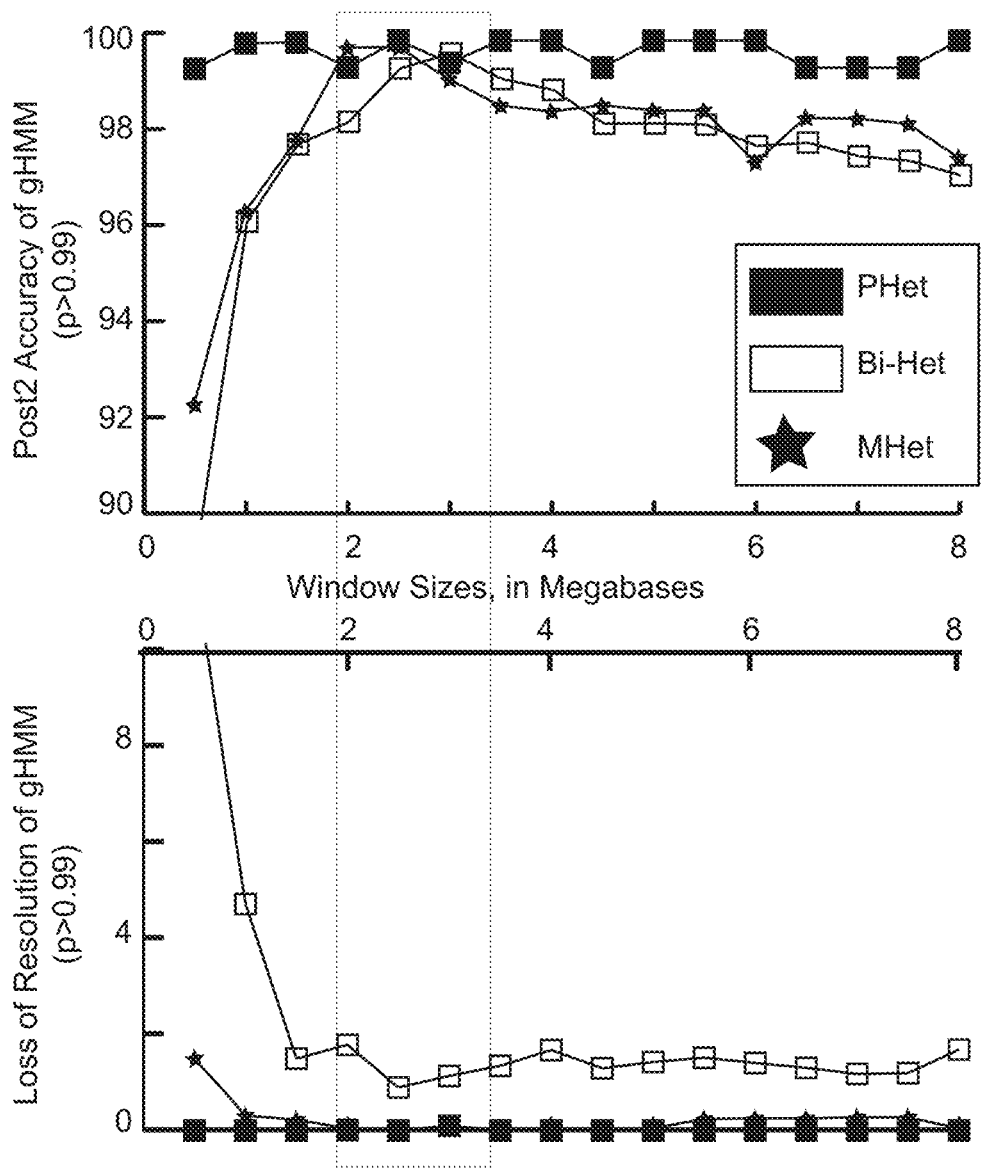
FIG. 6 shows a HMM-based highly accurate (>99%) fetal genetic content determination at 6× MPcfDNA, at all three types of fetal alleles in chromosome 1 (see FIG. 6A). For all three types of fetal alleles (MHet, PHet, Bi-het), gHMM generates >99% accuracy in fetal determination (top) with minimal loss of resolution (bottom) at an enumeration window sizes of 2-3 Mbs (grey strip). The accuracy defined in the plot is Post2 (post-hmm micro-switches and conflicts corrected) at a posterior threshold of 0.99 (FIG. 6B). The likelihood of the gHMM can be used as a proxy to accuracy.
In FIG. 6B(i), the likelihood of MHet (as described in FIG. 6A) is shown among different window sizes, and as expected, likelihood is maximum at a window size of 2-3 Mbs, corresponding well with the high accuracies in the same window range. The inset of FIG. 6B(i), reiterates the linear relationship between accuracy and likelihood—the higher the likelihood, the higher the accuracy.

Mbs window size (FIG. 6A). Three points emerge from this analysis. First, for this example, the window size that offers the best results can be different amongst the various allele types (e.g. 2.5 Mb window size is best for MHet and PHet, but a 3 Mbs window size is best for Bi-Het) (light gray vertical bar, FIG. 6A). This could be because the number of bases in the Bi-Het case is fewer than in the MHet and PHet cases, and therefore a larger window size may be needed for sufficient enumeration. Second, even with a 4-state HMM in Bi-het, the post2 accuracies are on par with the MHet and PHet cases using a 3 Mb window size. Third, PHet has accuracies of >99.5% regardless of the choice of window size, and this is likely due to the fact that there is only one recombination in the paternal haplotype, while 4 recombinations are manifested in the maternal haplotype (MHet, FIG. 3C). In this example, the sequence of fetal chromosome 1 was accurately determined (>99%) at different types of alleles, and at a minimal LOR at 6× sequencing of MPcfDNA.

Example 6: Using Likelihood Estimates to Guide the Optimization of HMM Parameters In another embodiment of the disclosure, likelihood estimates from the HMM are used as a proxy for accuracy. The likelihood estimate can direct the model towards optimal HMM parameters and therefore optimal accuracy and resolution, as true accuracy is often unknown. The mock-MPcfDNA is a special case as the parental and grandparental information is available as part of the 1000 Genomes Project, precisely annotating true accuracies. Analyses disclosed herein show that the likelihood and true accuracies correlate well. For instance, likelihood estimates from MHet alleles reach a maximum at a window size of 2-3 Mbs, as do the true accuracies (FIG. 6B), and follow a linear relationship with true accuracies (inset, FIG. 6B)—the higher the likelihood, the higher the true accuracies. When likelihood reaches a maximum, high HMM accuracy is achieved, which translates to higher post2 accuracies (FIG. 6B (ii)). Therefore, maximizing likelihood through variation of HMM parameters facilitates higher accuracies as measured by HMM, and post2, thereby generating improved final accuracy (A=99.77%) obtained from combining all types of alleles as shown in FIG. 7.

Example 7: Understanding the Impact of HMM Parameters on the Accuracy of Fetal Genetic Sequence Predictions It is important to understand the impact of HMM parameters such as standard deviation and transitional probabilities of the Gaussian model, and post-hmm window sizes (PSW) for correcting micro-switches and conflicts (post1, post2), on the predictive power of HMM, to determining a fetal sequence. First, standard deviation and transitional probability parameters were studied across different type of alleles to see their impact on accuracy. These analyses revealed that standard deviation had minimal impact on accuracy—for example, analyses from MHet alleles are shown in FIG. 6C. Similarly, optimal models (high accuracy and minimal LOR) were generated at multiple values (0.01 to 0.0001) of transitional probabilities (data not shown). These analyses suggest that standard deviation and transitional probabilities are not important parameters. Therefore, standard deviation was fixed close to empirical estimates of standard deviation from MPcfDNA enumerated allele fractions, and fixed transitional probabilities at 0.0001. These parameters however need to be tested in other chromosomes, fetal fractions other than 15% in MPcfDNA, or in other types of NIPT variations such as exome.

Example 8: Combining HMMs from Each Allele-Type to Build a Consensus Fetal Genome Determination While FIG. 6 shows results from MHet, PHet and Bi-het independently, FIG. 7 depicts the results from each allele type, as well as from combination steps. Specifically, the results from these three allele-types were combined to accurately determine the fetal genetic content of entire chromosome 1 at 6× MPcfDNA sequencing depth (final results A=99.77% and R=99.74%, FIG. 7). The main steps of this approach are a HMM for each allele-type, Post1 to correct micro-switches, and post2 to combine allele types that share information, i.e. MHet, Bi-het and PHet, Bi-het, to further correct micro-switches and resolve conflicts. This approach resulted in a final accuracy of 99.77% and a resolution of 99.74% for approximately 158,000 fetal alleles that were heterozygous in at least one parent in chromosome 1. As chromosomes are independently inherited, the process of fetal chromosome inference can be translated to fetal genome inference (as a genome is set of 22 independent autosomal chromosomes).

The results shown in FIG. 7 show that a post-HMM combination analysis (post1, post2) is important because chromosomes contain all types of alleles and only a combination analyses can result in the determination of a complete fetal genome, or exome, or any targeted locus. FIG. 7 shows results of an entire fetal chromosome prediction of one parameter set, and the parameters are depicted in every step of the process, which can be repeated to determine all chromosomes, thus the entire genome. FIG. 7 shows that: a) accuracy and resolution improve with each progressing step—for instance, in the case of MHet, HMM accuracy is 98.7%, while post1 is 99.62%, and post2 (Acm) is 99.8%; b) the Bi-hets are most difficult to predict possibly because of their 4-state nature but also because of fewer data points (bi-hets are manifested in approximately half of all alleles as with MHet and PHet); and c) the post-hmm window sizes (PSW) for post1 and post2 steps are dependent on the type of allele—a window of 500 Kb and 100 Kb is used for maternal and paternal alleles, respectively. Overall, fetal states for non-trivial 158,000 alleles were inferred with an accuracy and resolution of >99.7% (LOR of 0.3%) to determine the complete fetal chromosome 1, and by translation the complete fetal genome. In comparison to existing methods for fetal genome determination that generate an average accuracy of 95-99% at 40-70× sequencing depth, the disclosed method achieves 99.7% accuracy at 6× MPcfDNA sequencing depth. Even with a lower fetal fraction (e.g. 5-10%) in MPcfDNA, the disclosed methods, based on HaploSeq and HMM, will most likely require <10× MPcfDNA sequencing for fetal genome determination. Altogether, this example (as described in FIG. 7) demonstrates the high level of accuracy in determining a fetal genome from the disclosed multistep prediction model that utilizes enumeration, HMM protocol, efficient parameter optimization via an agnostic likelihood function, and post-HMM procedures.

Example 9: A Single 4-State HMM Instead of One HMM Per Allele-Type

Different HMM configurations are possible for prediction of a fetal genome. The utility of independent HMMs for each allele-type, and post-HMM combination analyses for combining predictions among allele-types has been shown above. Alternative HMM configurations were also studied. Specifically, a single 4-state HMM was implemented where all the allele-types were modeled together in a single instance. This single instance 4-state model, with the same parameter set (Standard deviation, Transition probabilities, etc.) as described in FIG. 7, generated an overall final accuracy of 99.05% and a resolution of 98.07%, in comparison to an accuracy and resolution of >99.7% in the independent configuration model (FIG. 7). This suggests that the model with independent configuration captures the data more precisely and allows for correction errors via post-hmm analyses, generating a higher accuracy and resolution than the 4-state single instance HMM. These results could be due to several factors. First, a 4-state single instance HMM models MHet, PHet and Bi-Hets via a 4-state and because in MHet and PHet only the maternal or paternal haplotype is informative, a 4-state model for these alleles might not capture the data effectively. Second, errors in one allele type may be forced on the other allele-types as all of them are modeled together. Therefore, it is believed that while different configurations of HMM are possible, it appears that an independent configuration of each allele type captures the essence of the MPcfDNA more precisely.

In addition, post1 and post2 accuracies were defined based on PSW (post window sizes) that were dependent on the allele types. Alternative methods such as discrete HMM to correct micro-switches and conflicts as in post1 and post2 can also be used in the disclosed methods. Both different configurations of HMM and post-HMM can be used as part of disclosed methods to generate a high-quality fetal determination.

The methods disclosed above, as exemplified by the determination of chromosome 1, can be repeated on all chromosomes, thus resulting in the determination of the entire fetal genome.

Example 10: A New Variant in NIPT: Determining SNV Genotype and Haplotype for Fetal -Omes Whereas whole genome fetal determination is informative and complete, in practical terms there can be limitations in terms of time and cost that can prevent someone from choosing to determine an entire fetal genome. Alternatively, a targeted region of a fetus can be determined. As an example, exons (coding regions) are distributed throughout the chromosome (and genome), and are collectively called an "exome". Exomes comprise approximately 2-3% of the genome. Also present in a genome are other types of "-omes". For example, an "-ome" can be a collection of common variants, a collection of cis-regulatory variants, or a collection of condition-specific genes, etc., that are distributed across a chromosome (or a genome). In some cases, determining a fetal -ome from MPcfDNA may be more practical. An exome, for example, contains information on all genes and therefore contains information pertaining to Mendelian diseases, which might be sufficient as a first pass before doing the more expensive fetal genome analyses. In other words, in the case of a fetal genome determination—using HaploSeq to determine chromosome-spanning haplotypes in parents (+<10× MPcfDNA), would result in a cost of "$5,000-$10,000", as per today's sequencing costs. For an exome, using Exome HaploSeq to determine chromosome-spanning exome haplotypes in parents (+50-100× MPcfDNA exome), would result in a cost of <$1,000, as exomes are only a minor subset of all bases in the genome.

Figure 2:
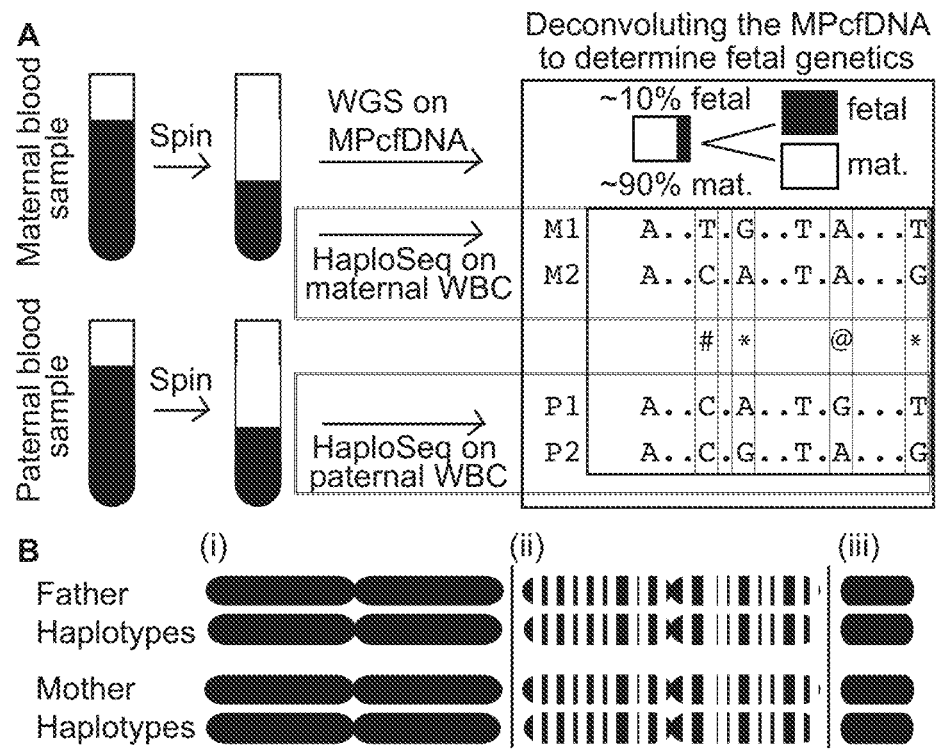
FIG. 2A depicts schematically how a fetal genotype and haplotype can be non-invasively determined. With simple blood draws from a mother and father, the fetal genotype and haplotype can be determined from sequencing the MPcfDNA. Specifically, maternal haplotypes inform fetal alleles that are derived from maternal-only heterozygous alleles (MHet, #), and similarly paternal haplotypes inform fetal alleles derived from paternal-only heterozygous alleles (PHet, @). In bi-parental heterozygous alleles (Bi-het, *), both haplotypes inform fetal genetic content.
FIG. 2B depicts chromosome-spanning parental haplotypes (i), chromosome-spanning parental -ome haplotypes (ii), and parental haplotypes of any locus (iii), as obtained from HaploSeq for fetal genome, exome, and locus analyses, respectively.

Despite a dramatic reduction in the number of fetal bases to be predicted (FIG. 2B(ii))—from 158,000 in the genome case (chromosome 1) to 3,500 in an exome case (chromosome 1), the disclosed enumeration, HMM and post-HMM methods can also be used for determining a fetal exome.

Figure 8A:
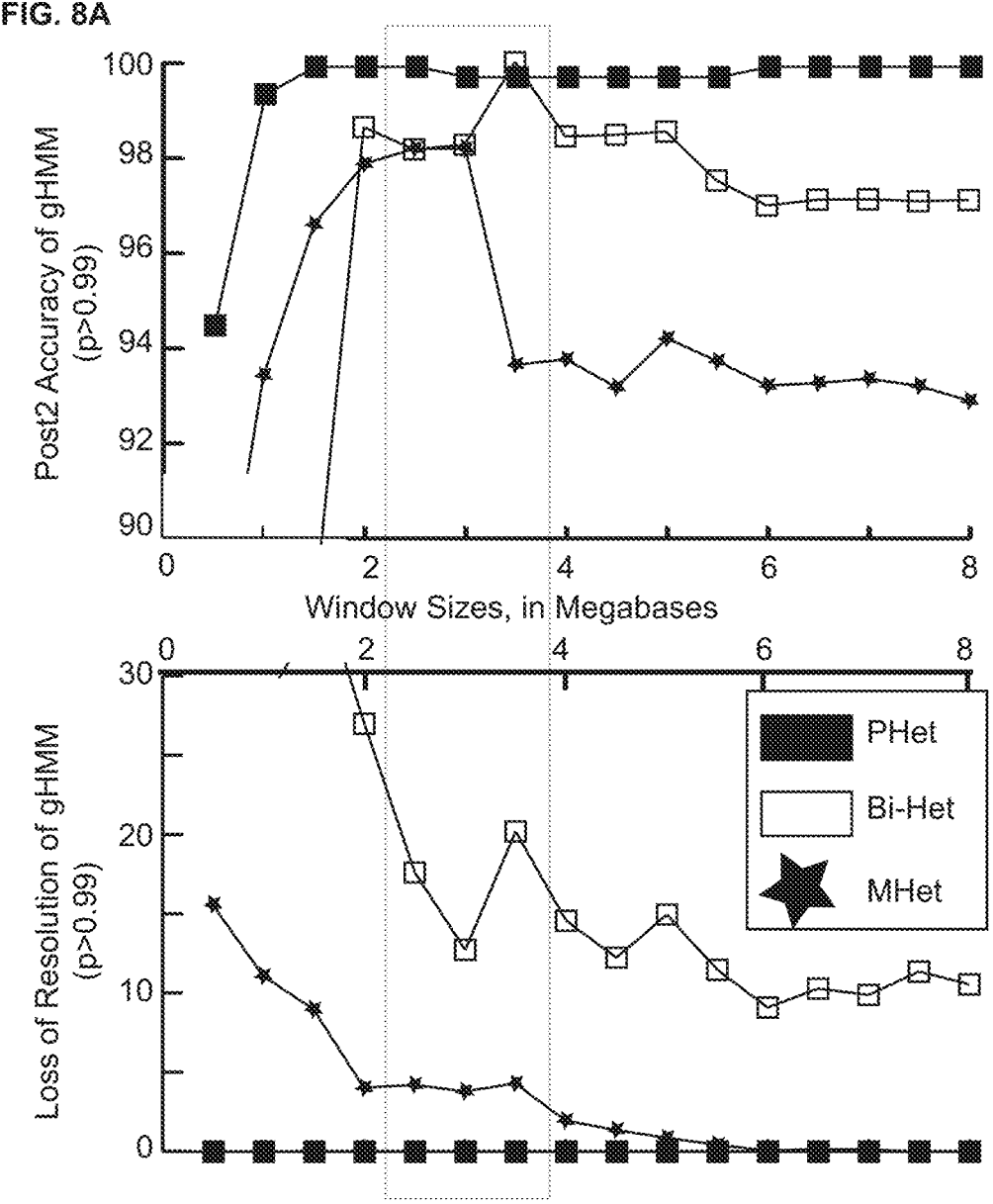
FIG. 8A shows that for all three types of fetal alleles (MHet, PHet, Bi-het), gHMM generates >98% accuracy in fetal exome determination (top). However, there is a significant loss of resolution (bottom) especially in B-Het fetal alleles. Regardless, enumeration window sizes of 2-4 Mbs (grey strip) generate the highest accuracy (>98%) at a reasonable loss of resolution (<5% for MHet, <20% for Bi-Het). The accuracy defined in the plot is the Post2 (post-hmm micro-switches and conflicts corrected) at a posterior threshold of 0.99 (FIG. 8B). As in FIG. 6B, with the genome case, the likelihood of the exome gHMM can also be used as a proxy to accuracy.
Figure 10:
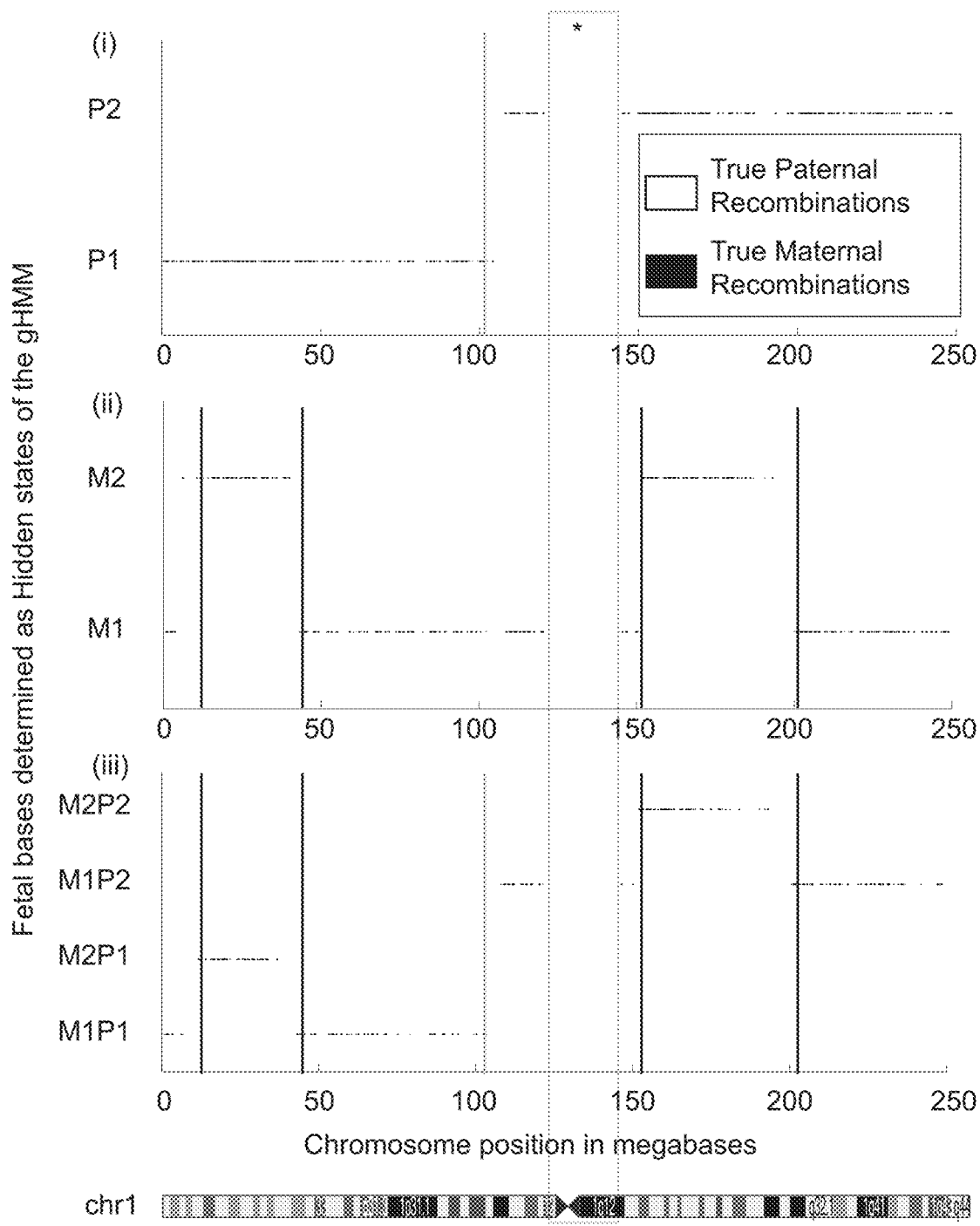
FIG. 10 shows the results of the fetal exome determination (from the final results in FIG. 9) visualized in terms of true parental recombination junctions. The overall objective of this method is to deconvolute a mixture MPcfDNA sample to determine the fetal genome and exome, and this is achieved by predicting parental recombination junctions to determine the fetal haplotype and genotype.

Owing to a reduced number of fetal alleles to be predicted in the case of fetal exomes, a higher sequencing depth of MPcfDNA (50-100×) might be required to gather a robust enumeration of allele frequencies that are needed for an accurate fetal exome determination. In addition to a higher depth of MPcfDNA sequencing, the use of chromosome-spanning parental exome haplotypes is important because exons are distributed across the entire chromosome and therefore, chromosome-spanning exome haplotypes alone can allow maximal enumeration for robust estimations of allele frequencies. A chromosome-spanning exome haplotype by definition also means no switch errors and therefore no fake recombinations—thereby enabling minimal MPcfDNA (50-100×) sequencing for fetal exome determination. For example, HaploSeq can generate chromosome-spanning exome parental haplotypes and therefore allows for the determination of fetal exomes, in addition to the determination of fetal genomes. In fact, this strategy can be applied to other -omes, as described above. To demonstrate the capabilities of the disclosed methods in determining a fetal exome, the following experiment was performed. 50× mock-MPcfDNA exome sequencing data (containing information only on exome sequences of MPcfDNA) was generated, and with the help of chromosome-spanning parental exome haplotypes from 1000Genomes (Paternal: GM12877, Maternal: GM12878, Child: GM12879), and the following disclosed methods were used to determine a fetal exome. The results are depicted in FIG. 8. FIG. 8 shows several things. First, the post2 accuracies among each allele type are >98%. However, due to higher recombinations in MHet and Bi-Het, the resolution is only modest (or the LOR is significantly higher than with the genome case (FIG. 6A)), especially in Bi-Hets (FIG. 8A). Second, an enumeration window size of 2-4 Mb work best among the different fetal alleles (FIG. 8A). As in the case of the fetal genome determination (FIG. 6B), likelihood estimates of the HMM model act as good proxies for accuracy and thereby can be used to direct the parameter optimization (FIG. 8B). As previously observed, the accuracy and resolution improves through the HMM and post-HMM combination process with a final fetal exome determination accuracy of 99.12% and a final resolution of 95.86% (LOR-4.14%) (FIG. 9). As impressive as these results are, sequencing higher than 50× might allow a reduced LOR and an even higher accuracy. Finally, in FIG. 10, the results from the fetal exome determination are shown in terms of true recombination locations. More specifically, FIG. 10 depicts the final fetal state predictions from FIG. 9, in the context of PHet (i), MHet (ii) and Bi-Het (iii). It is observed that the predicted exome states and the true recombination junctions agree very well, and as expected, most errors occur proximal to recombination junctions. Overall, these results for fetal exome determination follow similar principles and show a similar accuracy, as with the case of whole-genome fetal determination.

Example 11: Beyond Fetal SNVs (Single Nucleotide Variations)—Identification of Fetal Inherited Structural Variation Several available NIPT methods traditionally focus on determining aneuploidies such as trisomies in chromosomes 13, 18, and 21 to test for chromosomal abnormalities as observed in Patau syndrome, Edwards syndrome, or Down syndrome. These chromosomal abnormalities represent copy number variation (CNV) at the entire chromosome level. To this end, other NIPT approaches focus on SNV-based approaches to determine deletions such as DiGeorge syndrome. Therefore, existing approaches can determine chromosomal-level aneuploidies and smaller deletions.

Figure 11:
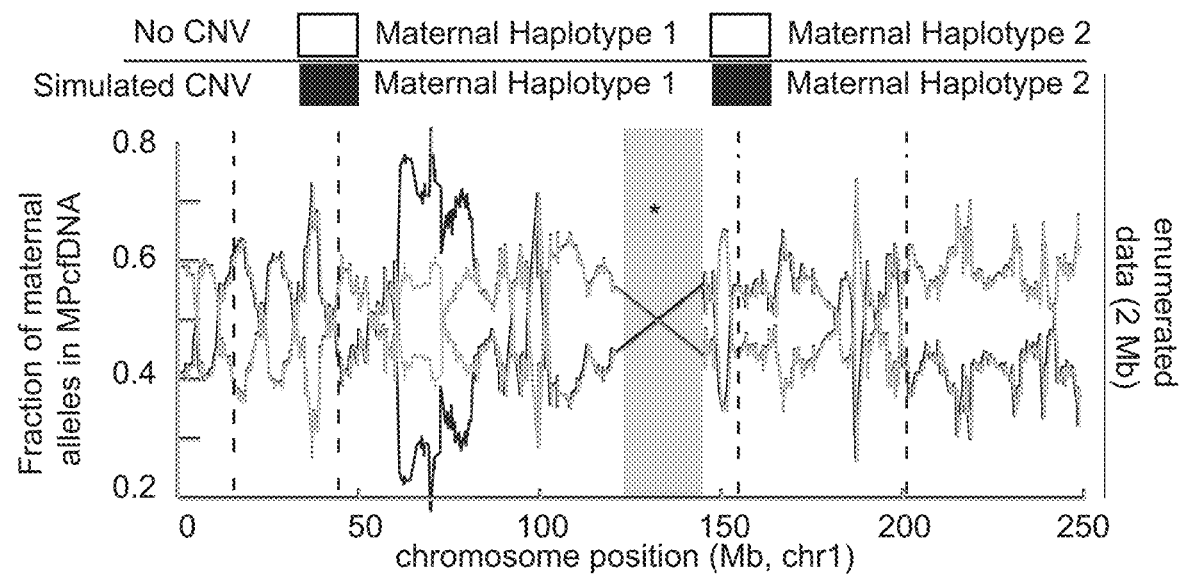
FIG. 11 shows the robust identification of fetal copy number variation (CNVs) in MPcfDNA. A simulated 20 Mb duplication event was introduced in the maternal chromosome 1: between approximately 60-80 Mb (light grey strip), and enumerated with 2 Mb windows. The transmitted CNV (manifested in black maternal haplotype M1) was detected in the MPcfDNA by a change in expected allele fractions of transmitted (from 0.575 to 0.72) and untransmitted (0.425 to 0.28) alleles (*denotes centromere).

In addition to accurately predicting a fetal genotype and haplotype to the level of SNVs, the disclosed enumeration HMM approach can also provide insight into fetal inherited CNVs and other types of structural variations, such as balanced structural variations (e.g. inversions). Furthermore, determination of a fetal CNV is possible both at the whole chromosome level and also at a specific region or locus. More generally, if the parental genomes contain an aneuploidy, a balanced structural variation, or a duplication CNV or deletion CNV, the disclosed methods will detect the transmission of such variation to the fetal genome. To demonstrate this, a 20 Mb duplication CNV was simulated in a maternal haplotype and the transmission of the duplication CNV to the fetal genome was detected by virtue of changes in the expected allele fractions (FIG. 11). Deletions or large duplications (such as trisomy) can be detected similarly. In the case of a balanced structural variation, the transmission of this type of variation can be detected by MPcfDNA read mapping strategies—as a balanced structural variation, such as an inversion is known to manifest a unique mapping signature (e.g. split-read phenomenon).

Example 12: A New Variant in NIPT: Determining SNV Genotype and Haplotype for Fetal Targeted Locus (or Loci)

Frequently it is of special interest to deconvolute a DNA mixture at a specific locus. Specifically, a targeted approach is appealing because it reduces sequencing costs, while providing the opportunity to sequence deeper to achieve a higher accuracy and resolution of fetal sequence determination. In one example, focusing on a 22q11.2 deletion in an NIPT sample can provide information related to DiGeorge syndrome. In a second example, the major histocompatibility complex (MHC) locus in humans is a major immune-response region and is studied in several disease conditions. For instance, if the fetal MHC locus (a 4 Mb locus in chromosome 6) is to be determined, this is done by leveraging parental locus-spanning haplotypes of MHC and utilizing the disclosed HMM-based methods to determine the fetal MHC locus using data from MPcfDNA. Because a method, for example, HaploSeq alone can determine locus-spanning parental haplotypes, the methods disclosed herein can leverage all SNVs within the locus to generate low-variance and robust estimates of allele fractions and fetal hidden states. Other approaches to generate haplotypes can create incomplete haplotypes that do not span the entire locus of interest and thereby creating switch errors and fake recombinations. As before mentioned, switch errors and fake recombinations complicate fetal sequence determination. A method such as HaploSeq, on the other hand, can minimize the MPcfDNA MHC sequencing required to determine a fetal MHC locus by allowing enumeration from all MHC SNVs and by simplifying the model via absence of fake recombinations. This rationale can be extended to any targeted locus or set of targeted loci, where the locus can be a gene or extended region, such as the MHC or KIRs (Killer Immunoglobin-like receptor region, chromosome 19). Overall, the disclosed enumeration, HMM, and post-hmm methods can deconvolute a MPcfDNA mixture to determine a fetal genome, an exome, or a targeted locus by leveraging parental haplotypes, as in the case of SNVs or structural variations.

Example 13: Determining Fetal Fraction

An important technical detail that enables this disclosure is the ability to define fetal fractions. More specifically, the mock MPcfDNA used in these analyses had 15% of fetal fraction. But in a real practical sample, estimating the percentage of fetal DNA in MPcfDNA will be key to define the expected allele fractions (e.g. 0.525, 0.425 in 15% fetal case). We can estimate the fetal fraction by collecting parental alleles that are both homozygous with one for reference allele and one for alternate allele (Bi-homUn: Mat Hom, Pat. Hom., unequal). At these alleles twice the fraction of paternal alleles to total read count in MPcfDNA defines the fetal fraction, as fetus inherits one half of its genome from the dad. That is, $f=2*p/(p+q)$, where f is the fetal fraction, p is read count from paternal allele and q is read count from maternal allele. With f being estimated, expected allele fractions as demonstrated in FIG. 5 can be tabulated and utilized in HMM to determine the fetal sequence.

Example 14: Knowledge of Both Parental Haplotypes Vs. the Availability of Only One Parental Haplotype for NIPT The methods described above require both parental haplotypes. In a case where only one parent's haplotype is available, enumeration may not be as effective and therefore may require increased sequencing of MPcfDNA for accurate determination of a fetal genome, an exome, or a targeted locus. Nevertheless, it is possible to determine a fetal sequence only with one parent's information. To this end, current NIPT methods detect de novo fetal aneuploidies and large CNVs via changes in expected MPcfDNA sequence information in the region comprising the CNV or aneuploidy. However, detecting de novo fetal SNVs is challenging, especially using the levels of low depth MPcfDNA sequencing recommended throughout the disclosure. More specifically, parental haplotypes provide limited information for detecting a fetal de novo variation, as by definition de novo variations are absent in parental genomes. In summary, the disclosed methods can determine any inherited fetal sequence by precise deconvolution of a MPcfDNA mixture sample.

Example 15: Beyond NIPT, Deconvolution in Cancer: Deconvoluting Patient's cfDNA to Determine Cancer-Associated Mutations for the Purpose of Cancer Diagnostic or Monitoring The methods disclosed herein can be also used to deconvolute other mixture samples besides a mixture sample MPcfDNA used in NIPT, where the disclosed methods utilize a HMM-based approach and leverage parental haplotypes. Mixture samples are common in molecular oncology and transplantation, and other areas of medicine. In oncology, recent efforts have begun to use cell-free tumor DNA (ctDNA) manifested in a patient's blood plasma, urine or other bodily fluid, as a means for non-invasive detection of cancer-associated mutations. Because ctDNA assays, also referred to as liquid biopsy assays (LBAs), offer direct measurements of genetic material that are associated with the diagnosis or progression of cancer, these assays enable accurate screening and monitoring of a wide-range of cancer types, obviating the need for invasive tissue biopsies. However, because the fraction of ctDNA present in a patient's cfDNA from a liquid biopsy sample can be as low as 0.01% in early-stage cancers, and is rarely as high as 10% in late-stage cancers, developing highly accurate methods for cfDNA based cancer analyses is challenging. Current commercial methods focus on highly sensitive methods such as digital droplet based PCR (ddPCR) or ultra-deep DNA sequencing (15,000-40,0000× depth) to detect a specific single nucleotide mutation among a pre-defined gene or locus that is recursively associated with a particular cancer type, but these methods are limited to single nucleotide mutations and smaller structural variations. For larger structural variations (LSV), such as large CNV and aneuploidies, deep sequencing (>10,000×) of cfDNA covering LSVs is needed, which is cost-prohibitive. Also, there are very few methods focusing on LSVs. LSVs are considered a hallmark of cancer and therefore detecting a LSV via minimal cfDNA sequencing, enables the development of a clinical method for the early detection, monitoring, and/or surveillance of a particular type of cancer.

Figure 12A:
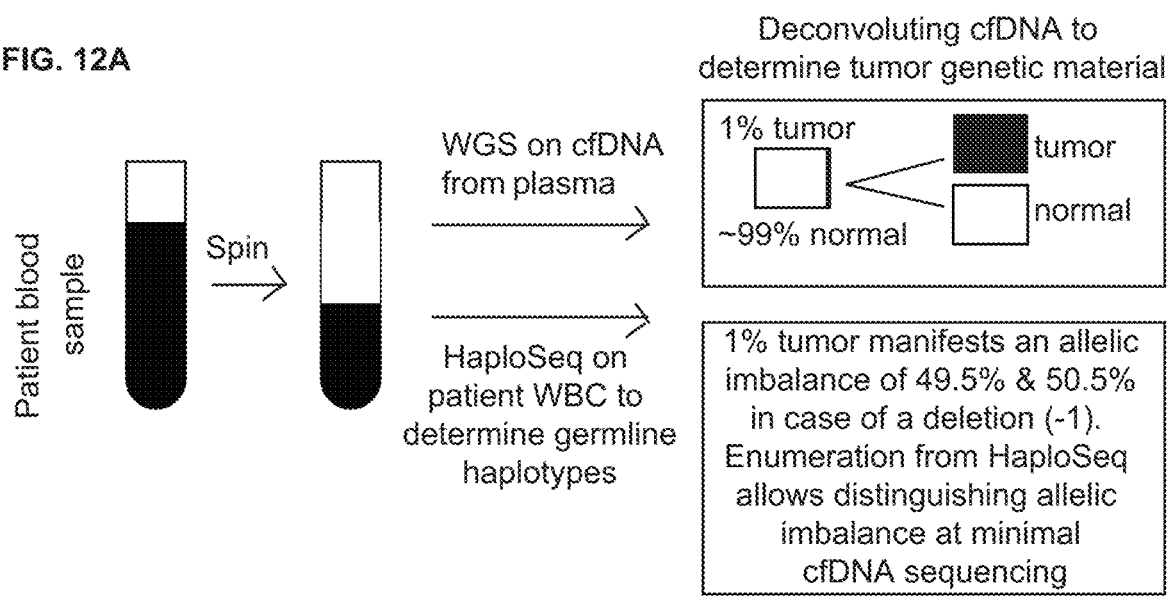
FIG. 12 shows how the disclosed methods can deconvolute a patient's cfDNA to determine the genetic content of a patient's tumor (FIG. 12A). With a simple blood draw from the patient, the genetic content of the tumor can be determined from cfDNA, as it contains DNA from both normal cells and tumor cells. While the genetic content of the tumor can contain different types of variations, large structural variations (LSVs) are considered the hallmark of cancer. LSVs can be a deletion or duplication event, and on average, tumors are known to contain 8 LSVs. For example, deletion based LSV's (denoted as −1) can be determined via an allelic imbalance of 49.5% to 50.5%, assuming a 1% tumor fraction in cfDNA. However, differentiating imbalances of 49.5% to 50.5% requires deep sequencing of cfDNA. Generating long germline haplotypes enables enumeration of SNV alleles in the LSVs that are common between tumor and normal cells, to cumulatively gather allele fraction evidence from throughout the LSV on the same germline haplotype, thereby enabling detection of tumor-associated LSVs from minimal sequencing of cfDNA.
FIG. 12B and FIG. 12C describe how the disclosed methods can be used to detect 8 chromosome-arm level LSVs.

Extensive efforts from groups such as The Cancer Genome Atlas (TCGA) have demonstrated that LSVs in tumor genomes tend to be large chromosome arm level copy number changes. In fact, there are estimated to be on average 8 such LSVs in the average cancer genome. In this disclosure, long haplotypes, for example, chromosome-spanning germline haplotypes from HaploSeq are leveraged to enumerate and therefore minimize the amount of cfDNA sequencing required to detect LSVs (FIG. 12A). More specifically, assuming that there is 1% tumor DNA in a patient's cfDNA, a LSV deletion in a tumor causes an allelic imbalance of 49.5:50.5 in the sequence obtained from the cfDNA. However, distinguishing such a small allelic imbalance needs deep sequencing of cfDNA. By leveraging long germline haplotypes and enumerating over SNVs from within the LSV that fall in the same haplotype, one can obtain low-variance and robust estimates of allele fractions. This enables detection of cancer-associated LSVs from minimal cfDNA sequencing. It is important to have long haplotypes that entirely cover an LSV, and because there are multiple LSVs (an average of 8), only chromosome-spanning germline haplotypes (for example, as obtained from HaploSeq) can guarantee the absence of switch errors in LSV regions. Indeed, chromosome-spanning haplotypes (for example, as obtained from HaploSeq) can minimize the amount of cfDNA sequencing in the case of both a deletion LSV (FIG. 12B(i)) or a duplication LSVs (FIG. 12C(i)), and this is especially striking in cases of a lower tumor fraction (0.1-1%), as depicted in (FIG. 12B(ii), and FIG. 12C(ii)). Together, chromosome-spanning haplotypes (for example, as obtained from HaploSeq) allow minimal sequencing of cfDNA to detect a tumor associated LSV. This is a striking reduction from hundreds of thousands in sequencing depth to <5× cfDNA sequencing depth, in the case of deletions at a 1% tumor fraction, and similar reductions in duplication and other cases. To further minimize cfDNA sequencing depth, traditional depth-of-coverage based approaches can be combined with HaploSeq-based enumeration approach. In summary, the determination of chromosome-spanning and generally long germline haplotypes allows maximal enumeration which can be inputted in to an HMM model to deconvolute a mixed cfDNA sample to detect tumor-associated LSV.

A variant of the above problem is utilizing long germline haplotypes of -omes (for example, chromosome-spanning germline haplotypes of -omes) for detection of tumor-associated mutations in cfDNA. Chromosome-spanning germline haplotypes of -omes are cost-effective in comparison to obtaining chromosome-spanning germline haplotypes, but might be able to offer sufficient enumeration for detecting tumor-associated mutations, especially in the case of LSVs. Similarly, locus-spanning germline haplotypes will be sufficient when a tumor-associated mutation needs to be detected at a specific locus.

Example 16: Beyond NIPT and Cancer: Deconvoluting Transplantation Recipient's cfDNA to Quantify Donor DNA for Transplantation Monitoring and Transplantation Outcome Predictions The methods disclosed herein can also be used to deconvolute mixture samples that are obtained during a transplantation procedure. For instance, from a simple blood draw taken from a recipient of transplantation, one can construct germline haplotypes from the patient's WBCs. Then from plasma, cfDNA (Recipient cfDNA (RcfDNA)) can be obtained that contains DNA from both the donor and the recipient. Quantifying the amount of donor DNA in RcfDNA will allow a health care professional caring for the transplant recipient to monitor the progress of the transplantation and determine the outcome of the transplantation procedure. Because a donor (of an organ, for example) can be related or unrelated to the recipient, several strategies can be taken. In the case of a genetically related donors (e.g. mother of recipient), a strategy similar to NIPT can be performed. For instance, understanding that parental genomes have recombined to result in a child's (recipient) genome, knowledge of recipient germline haplotypes allows for the quantification of a related donor's DNA in RcfDNA. In fact, knowledge of recipient germline haplotypes from HaploSeq can allow maximal enumeration, which will in turn minimize the amount of RcfDNA required to quantify the donor's DNA. In a similar case, if the donor is unrelated to the recipient, an assumption that the donor's and recipient's haplotypes are different, and the knowledge of recipient germline haplotypes will enable quantification of the donor's DNA. Such analyses can be performed genome-wide or restricted to immune-response locus such as KIRs or MHCs. This is possible because of the use of chromosome-spanning haplotypes (for example, as obtained by HaploSeq or chromosome-spanning haplotypes of -omes, e.g. as obtained by Exome HaploSeq) for genome-wide analyses of RcfDNA, as well as the use of targeted locus-spanning haplotypes of MHC/KIR for analyzing MHC/KIR regions in RcfDNA. As an example, KIR/MHC germline locus-spanning haplotypes can be obtained from a recipient's WBCs and then KIR/MHC regions can be captured from RcfDNA. This will allow the understanding of what fraction of RcfDNA is from the donor MHC/KIR versus the recipient MHC/KIR. A locus-spanning MHC/KIR germline haplotype allows for maximal enumeration (more SNVs in locus, more enumeration), and a locus-spanning haplotype mean no switch errors within the locus. Therefore, chromosome-spanning haplotypes or entire locus-spanning haplotypes are important to maximize enumeration, in applications of NIPT, cancer, and transplantation.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for non-invasive determination of fetal genetic content in a maternal cell-free nucleic acid sample, comprising:

obtaining a maternal cellular sample comprising a set of chromosomes having genomic DNA and obtaining maternal chromosome-spanning haplotypes from the maternal sample;

obtaining a paternal cellular sample comprising a set of chromosomes having genomic DNA, and obtaining paternal chromosome-spanning haplotypes from the paternal sample, wherein the maternal and/or paternal haplotypes are obtained using a method comprising proximity ligation and shotgun sequencing;

obtaining a maternal cell-free nucleic acid sample and determining sequences of the maternal cell-free nucleic acid sample, wherein the sequences are determined using whole genome sequencing at a sequencing depth of less than 10×;

determining allele fractions of both transmitted and untransmitted maternal and transmitted and untransmitted paternal alleles from the sequences of the maternal cell-free nucleic acid sample using the maternal and paternal chromosome-spanning haplotypes and neighboring allele fractions in an enumeration window; and inputting the determined allele fractions into a Hidden Markov Model (HMM) to determine fetal genetic content.

2. The method of claim 1, wherein the fetal genetic content is a whole fetal genome.

3. The method of claim 1, wherein an enumeration window size is about 100 kilobases to about 20 megabases.

4. The method of claim 1, wherein the fetal genetic content is genotypes and haplotypes.

5. The method of claim 1, wherein determining sequences is at a sequencing depth of about 1×, 2×, 3×, 4×, 6×, or 8× for the maternal cell-free nucleic acid sample.

6. The method of claim 1, wherein an enumeration window size is about 2 megabases.

* * * * *